United States Patent
Baraldi et al.

(10) Patent No.: US 7,064,204 B2
(45) Date of Patent: Jun. 20, 2006

(54) PHARMACEUTICALLY ACTIVE COMPOUNDS HAVING A TRICYCLIC PYRAZOLOTRIAZOLOPYRIMIDINE RING STRUCTURE AND METHODS OF USE

(75) Inventors: Pier Giovanni Baraldi, Ferrara (IT); Pier Andrea Borea, Ferrara (IT)

(73) Assignee: King Pharmacueticals Reserch and Development, Inc., Cary, NC (US)

( * ) Notice: Subject to any disclaimer, the term of this patent is extended or adjusted under 35 U.S.C. 154(b) by 0 days.

(21) Appl. No.: 10/452,788

(22) Filed: May 30, 2003

(65) Prior Publication Data

US 2004/0039004 A1 Feb. 26, 2004

Related U.S. Application Data

(60) Provisional application No. 60/384,809, filed on May 30, 2002.

(51) Int. Cl.
*C07D 487/14* (2006.01)
*A61K 31/519* (2006.01)
*A61K 31/5377* (2006.01)

(52) U.S. Cl. ............... 544/251; 544/115; 514/233.2; 514/252.16; 514/267

(58) Field of Classification Search ............ 514/233.2, 514/252.16, 267; 544/115, 251
See application file for complete search history.

(56) References Cited

U.S. PATENT DOCUMENTS

| 6,407,236 | B1 * | 6/2002 | Baraldi et al. | 544/251 |
| 6,448,253 | B1 * | 9/2002 | Baraldi | 514/267 |
| 6,630,475 | B1 * | 10/2003 | Neustadt et al. | 514/257 |
| 2003/0212059 | A1 * | 11/2003 | Boyle et al. | 514/217.06 |

FOREIGN PATENT DOCUMENTS

| WO | WO 95/01356 | 1/1995 |
| WO | WO 97/05138 | 2/1997 |
| WO | WO 00/15231 | 3/2000 |
| WO | WO 01/92264 A1 | 6/2001 |

OTHER PUBLICATIONS

Luo Yan; Joachim C. Burbiel; Astrid Maaβ; Christa E. Müller, Expert Opinion on Emerging Drugs 2003, vol. 8, No. 2, pp. 537 - 576.*

Pier Giovanni Baraldi; Allan R Moorman; Mojgan Aghazadeh Tabrizi; MariaGiovanna Pavani; Romeo Romagnoli, Expert Opinion on Therapeutic Patents, 2004, vol. 14, No. 1, pp. 71-79.*

P.G. Baraldi; B. Cacciari; R. Romagnoli; G. Spalluto, Expert Opinion on Therapeutic Patents, 1999, vol. 9, No. 5, pp. 515-527.*

Popoli, P. et al, Curr. Med. Chem., 2004, 4, pp. 1-11.*

Kiec-Kononowicz, K. et al, Pure Appl. Chem., 73, 2001, pp. 1411-1420.*

Hess, Sonja, Expert Opinion Ther. Patents, 2001, 11, pp. 1533-1561.*

F. Gatta, et al., "Synthesis of imidazo[1,2-c]pyrazolo[4,3-e]pyrimidines, pyrazolo [4,3-e]1,2,4-triazolo[1,5-c]pyrimidines and 1,2,4-triazolo[5,1-i]purines: new potent adenosine $A_2$ receptor antagonists," European Journal of Medicinal Chemistry (1993), vol. 28, Nos. 7/8, pp. 569-576, XP009002008.

P. Baraldi, et al., "Pyrazolo[4,3-e]1,2,4-triazolo[1,5-c]pyrimidine Derivatives as Highly Potent and Selective Human $A_3$ Adenosine Receptors Antagonists: Influence of the Chain at the $N^8$ Pyrazole Nitrogen," Journal of Medicinal Chemistry (2000), vol. 43, No. 25, pp. 4768-4780, XP-002256635.

P. Baraldi, et al., Design, Synthesis, and Biological Evaluation of $C^9$ —and $C^2$ Substituted Pyrazolo [4,3-e]-1,2,4-trizolo [1,5-c]pyrimidines as new $A_{2A}$ and $A_3$ Adenosine Receptor Antagonists, Journal of Medicinal Chemistry (2003), vol. 46, No. 7, pp. 1229-1241, XP-002256636.

A copy of the Annex to Form PCT/ISA/206 (Communication Relating to the Results of the Partial International Search), dated Oct. 28, 2003.

P. Baraldi, et al., "Synthesis Biological Activity, and Molecular Modeling Investigation of New Pyrazolo [4,3-e]-1,2,4-triazolo[1,5-c]pyrimidine Derivatives as Human $A_3$ Adenosine Receptor Agonists", Journal of Medicinal Chemistry, vol. 45, No. 4, Feb. 14, 2002, pp. 770-780, XP002271430.

A copy of the International Search Report dated Mar. 29, 2004, issued in corresponding application No. PCT/US03/17313.

* cited by examiner

*Primary Examiner*—Thomas C. McKenzie
(74) *Attorney, Agent, or Firm*—Jones Day

(57) ABSTRACT

New compounds having a tricyclic pyrazolotriazolopyrimidine ring structure are provided and methods of using those compounds for a variety of therapeutic indications.

3 Claims, No Drawings

PHARMACEUTICALLY ACTIVE COMPOUNDS HAVING A TRICYCLIC PYRAZOLOTRIAZOLOPYRIMIDINE RING STRUCTURE AND METHODS OF USE

CROSS-REFERENCE TO RELATED APPLICATIONS

This application claims priority to U.S. Provisional Applications 60/384,809 filed May 30, 2002, which is incorporated herein by reference in its entirety.

BACKGROUND TO THE INVENTION

1. Field of the Invention

The present invention relates to compounds having a tricyclic pyrazolotriazolopyrimidine ring structure which possess antagonist activity for adenosine receptors, particularly the $A_1$, $A_{2A}$, $A_{2B}$, $A_3$ adenosine receptor subtypes. In particular, the invention relates to new compounds having a tricyclic pyrazolotriazolopyrimidine ring structure, methods of synthesis for those compounds, and methods of using those compounds for modulation of biological function in the nervous, cardiovascular, renal and immune systems of a mammal and methods for treatment of a mammal suffering from or susceptible to diseases or disorders associated with adenosine bio-activity in the nervous, cardiovascular, respiratory, renal and/or immune systems of the mammal.

2. Background

Adenosine, an endogenous modulator of a wide range of biological functions in the nervous, cardiovascular, respiratory, renal, and immune systems, interacts with at least four cell surface receptor subtypes classified as $A_1$, $A_{2A}$, $A_{2B}$ and $A_3$. These receptor subtypes belong to the superfamily of G protein-coupled receptors and have been cloned from several animal species.

In the past ten years, great efforts by medicinal chemists and pharmacologists have been devoted to the design of potent and selective ligands for $A_{2A}$ and $A_3$ receptors. Thus, the pyrazolotriazolopyrimidines SCH 58261 (5-amino-7-(2-phenylethyl)-2-(2-furyl)pyrazolo[4,3-e]1,2,4-triazolo[1,5-c]pyrimidine), SCH 63390 (5-amino-7-(3-phenylpropyl)-2-(2-furyl)pyrazolo[4,3-e]1,2,4-triazolo[1,5-c]pyrimidine) and related compounds that possess hydrophilic groups at the para and ortho positions of the aromatic ring have been found to be potent and selective adenosine $A_{2A}$ antagonists, and SCH 58261 is widely used as a tool for characterizing the adenosine $A_{2A}$ receptor subtype. See, for example, (1) Baraldi, P. G. et al, *Curr. Med: Chem.;* 1995, 2, 707–722; (2). Baraldi, P. G. et al., *J. Med. Chem.* 1998, 41, 2126–2133; (3). Baraldi, P. G.; et al., *J. Labeled Compds. Radiopharm.* 1996, XXXVIII, 725–732; and (4). Zocchi, C et al., *Br. J. Pharmacol.* 1996, 117, 1381–1386. At the same time, different classes of compounds have been reported to be selective $A_3$ receptor antagonists (eight classes with non-xanthine structure, including dihydropyridine and pyridine analogs, flavonoid, isoquinoline and triazoloquinazoline derivatives, triazolonaphthiridine and thiazolopyrimidine analogs). The best results in terms of $A_3$-antagonism were obtained with 5-N-(substituted phenylcarbamoyl)amino-8-substituted-2-(2-furyl)pyrazolo[4,3-e]-1,2,4-triazolo[1,5-c]pyrimidines, which are substituted on the phenyl ring of the phenyl carbamoyl moiety with a para-methoxy group or a para-chloro group ((1) Baraldi, P. G. et al., *Trends Pharmacol. Sci.* 2000, 21, 456–459; (2). Braldi, P. G., et al., *J. Med. Chem.* 1999, 42, 4473–4478; and (3). Varani, K.; et al., *Mol. Pharmacol.* 2000, 57, 968–975).

Attempts to modulate the metabolism of adenosine, thereby increasing the endogenous levels have been examined. In rodents, the use of adenosine deaminase inhibitors to prevent the rapid deamination of adenosine to inosine was shown to greatly enhance the effectiveness of spinal morphine in reducing allodynia. A similar effect was observed with the intrathecal administration of nucleoside transport inhibitors that slow or prevent the cellular uptake of circulating adenosine. Adenosine kinase inhibitors, which prevent the phosphorylation of adenosine to adenosine monophosphate, have also been reported as effective (Lynch et al, *Eur. J. Pharmacol.* 364: 141–146 (1999); Kowaluk et al, *J. Pharmacol. Exp. Ther.* 295: 1165–1174 (2000); Suzuki et al, *Br. J. Pharmacol.* 132: 1615–1623 (2001); Zhu et al, *Brain Res.* 905: 104–110 (2001)). All of these approaches act by increasing the concentration of adenosine available to the adenosine $A_1$ receptor.

Investigations of other modulation of adenosine receptors have been reported in Bruns et al., *Mol. Pharmacol.* 38: 939–949 (1990); Bruns et al., *Mol. Pharmacol.* 38: 950–958 (1990); Bruns et al., *Mol. Pharmacol.* 38: 939–949, 950–958 (1990), Leung et al, *Naunyn-Schmied. Arch. Pharmacol.* 352: 206–212 (1995); Baraldi, U.S. Pat. No. 5,939,432; Baraldi et al, *Bioorg. Med. Chem. Lett.* 10: 1953–1957 (2000); van der Klein et al, *J. Med. Chem.* 42: 3629–3635 (1999); Kourounakis et al, *Drug Dev. Res.* 49: 227–237 (2000); and Tranberg et al, *J. Med. Chem.* 45: 382–389 (2002)).

SUMMARY OF THE INVENTION

We now provide compounds having a tricyclic pyrazolotriazolopyrimidine ring structure useful as ligands of the family of adenosine receptors, particularly the adenosine $A_1$, $A_{2A}$, $A_{2B}$, and $A_3$ receptors, and methods of preparation and use thereof are disclosed. Such compounds may be used to modulate biological responses in the nervous, cardiovascular, renal, respiratory, and immune systems of a mammal, particularly a human.

More particularly, we now provide compounds having a tricyclic pyrazolotriazolopyrimidine ring structure that will be useful for a variety of therapeutic applications, including cardiovascular diseases such as congestive heart failure, radiation induced fibrosis, liver cirrhosis, asthma, chronic obstructive pulmonary disease, intestinal inflammation, diabetes, Parkinson's disease or Parkinsonism, inflammatory diseases, particularly those inflammatory diseases involving mast cell degranulation, severe allergic reactions (including bee stings, food allergies, seasonal allergies, e.g., rhinitis), cancers in which the expression level of adenosine $A_3$ receptor is elevated, and glaucoma.

We have discovered that the affinity at adenosine receptors to the compounds of the invention, e.g., substituted compounds having a tricyclic pyrazolotriazolopyrimidine ring structure, are very potent antagonists on adenosine receptors particularly the $A_1$, $A_{2A}$, $A_{2B}$, $A_3$ adenosine receptors. Compounds of the invention possessing substitution at the 9-position of the tricyclic pyrazolotriazolopyrimidine ring structure exhibit good binding affinity to the $A_1$, $A_{2A}$, $A_{2B}$, $A_3$ adenosine receptors and are non-selective antagonists for a specific adenosine receptor, i.e., compounds substituted at the 9-position typically bind to each of the $A_1$, $A_{2A}$, $A_{2B}$, $A_3$ adenosine receptors with similar binding affinities.

Compounds having a tricyclic pyrazolotriazolopyrimidine ring structure of the invention are substituted at the 2 and 5 ring positions of the ring system and have at least one additional ring substitutent at the 7, 8, or 9 ring position. Typically the 5 position is substituted with an optionally substituted amino group. As referred to herein, "Compounds having a tricyclic pyrazolotriazolopyrimidine ring structure" refers to the compounds comprising a core ring structure of the formula:

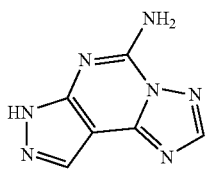

In certain preferred aspects of the invention, compounds having a tricyclic pyrazolotriazolopyrimidine ring structure have a substantially coplanar structure.

In further aspects of the invention, the compounds having a tricyclic pyrazolotriazolopyrimidine ring structure may comprise at least one additional ring structure, preferably an aromatic ring attached to the tricyclic pyrazolotriazolopyrimidine ring structure at the 2 position. Suitably, such an aryl or heteroaryl ring will have one or more heteroatoms or functional groups capable of hydrogen bonding to complementary groups on the adenosine receptor site.

Preferred compounds having a tricyclic pyrazolotriazolopyrimidine ring structure of the invention include those of the following Formulae I and II:

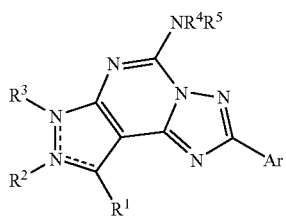

Formula II

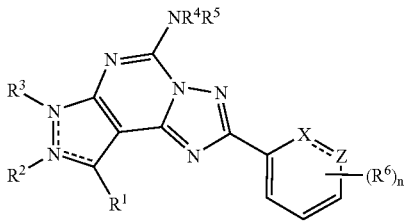

wherein:

Ar is an optionally substituted aryl or an optionally substituted heteroalicyclic or heteroaromatic group;

X is O, S, N, or $CR^6$;

Z is $CR^6$ when X is either N or $CR^6$, or

Z is absent when X is O or S;

n is an integer of from 1 to about 5;

$R^1$ is selected from the group consisting of hydrogen, halogen, cyano, amino, nitro, thio, optionally substituted alkyl, optionally substituted alkenyl, optionally substituted alkynyl, optionally substituted alkoxy, optionally substituted alkylamino, optionally substituted dialkylamino, optionally substituted arylamino, optionally substituted diarylamino, optionally substituted (aryl)(alkyl)amino, optionally substituted alkylthio, optionally substituted alkylsulfinyl, optionally substituted alkylsulfonyl, optionally substituted alkanoyl, optionally substituted carbocyclic aryl, optionally substituted aralkyl, and an optionally substituted heteroalicyclic or heteroaromatic;

$R^2$ and $R^3$ are absent or independently selected from the group consisting of optionally substituted alkyl, optionally substituted alkenyl, optionally substituted alkynyl, optionally substituted aralkyl, optionally substituted alkanoyl, optionally substituted carbocyclic aryl, and an optionally substituted heteroalicyclic or heteroaromatic;

$R^4$ and $R^5$ are independently selected from the group consisting of hydrogen, metabolically cleavable group, optionally substituted alkyl, optionally substituted alkenyl, optionally substituted alkynyl, optionally substituted carbocyclic aryl, optionally substituted alkanoyl, optionally substituted aranoyl, and an optionally substituted heteroalicyclic or heteroaromatic; and pharmaceutically acceptable salt thereof.

each $R^6$ is independently selected from the group consisting of hydrogen, halogen, cyano, amino, nitro, thio, carboxylate, optionally substituted alkyl, optionally substituted alkenyl, optionally substituted alkynyl, optionally substituted alkoxy, optionally substituted alkylamino, optionally substituted dialkylamino, optionally substituted arylamino, optionally substituted diarylamino, optionally substituted (aryl)(alkyl)amino, optionally substituted alkylthio, optionally substituted alkylsulfinyl, optionally substituted alkylsulfonyl, optionally substituted alkanoyl, optionally substituted carbocyclic aryl, optionally substituted aralkyl, optionally substituted carboxamide, optionally substituted carboxy aralkyl, optionally substituted benzoate, and an optionally substituted heteroalicyclic or heteroaromatic; and pharmaceutically acceptable salt thereof.

Preferred compounds of the invention exhibit good activity in an $A_1$, $A_{2A}$, $A_{2B}$, or $A_3$-adenosine receptor antagonist assay. Compounds of the invention may either be selective for one or more adenosine receptor subtypes or they may be non-selective. Typically 9-substituted compounds of the invention are non-selective. Antagonist activity at the $A_1$-adenosine receptor is measured by a cAMP enhancement assay, as such assay is exemplified in Example 2, which follows. References herein to a "cAMP enhancement assay" are defined to mean the assay of the protocol specified in Example 2, which follows. Particularly preferred compounds will provide a 10 percent increase in cAMP activity relative to control at a test compound concentration of 10 µM in such a defined cAMP enhancement assay, more preferably a 30 or 40 percent increase in cAMP activity relative to control at a test compound concentration of 10 µM.

The invention further provides therapeutic methods, particularly methods for treating a mammal suffering from or susceptible to (prophylactic therapy) to cardiac diseases or disorders including congestive heart failure; neurological disease or injury; sleep disorders, diabetes; various inflammatory diseases and conditions (particularly those inflammatory diseases involving mast cell degranulation); radiation induced fibrosis; liver cirrhosis; asthma; chronic obstructive pulmonary disease; intestinal inflammation; diabetes; Parkinson's disease or Parkinsonism; severe allergic reactions (including bee stings, food allergies, seasonal allergies, e.g., rhinitis); cancers in which the expression level of the adenosine $A_3$ receptor is elevated; and glaucoma. The therapeutic methods of the invention in general comprise administering to a mammal, such as a primate, particularly a human, a therapeutically effective amount of a compound having a tricyclic pyrazolotriazolopyrimidine ring structure, such as a compound of the above Formulae I or II as well as any of Formulae III through XI as those formulae are defined below.

Therapeutic methods of the invention in general comprise administering an effective amount of one or more compounds having a tricyclic pyrazolotriazolopyrimidine ring structure as disclosed herein to a mammal in need thereof, particularly a primate such as a human. Preferred fused thienyl compounds include those of Formulae I through XI as those formulae are defined herein.

In a further aspect, the invention provides use of a compound having a tricyclic pyrazolotriazolopyrimidine ring structure, including a compound of any one of Formulae I through XI for the treatment or prevention (including prophylactic treatment) of a disease or condition as disclosed herein, including cardiac diseases or disorders including congestive heart failure; neurological disease or injury; sleep disorders, diabetes; various inflammatory diseases and conditions (particularly those inflammatory diseases involving mast cell degranulation); radiation induced fibrosis; liver cirrhosis; asthma; chronic obstructive pulmonary disease; intestinal inflammation; diabetes; Parkinson's disease or Parkinsonism; severe allergic reactions (including bee stings, food allergies, seasonal allergies, e.g., rhinitis); cancers in which the expression level of adenosine $A_3$ receptor is elevated; and glaucoma.

In a yet further aspect, the invention provides use of a compound having a tricyclic pyrazolotriazolopyrimidine ring structure, including a compound of any one of Formulae I through XI for the preparation of a medicament for the treatment or prevention (including prophylactic treatment) of a disease or condition as disclosed herein, including cardiac diseases or disorders including congestive heart failure; neurological disease or injury; sleep disorders, diabetes; various inflammatory diseases and conditions (particularly those inflammatory diseases involving Mast Cell degranulation); radiation induced fibrosis; liver cirrhosis; asthma; chronic obstructive pulmonary disease; intestinal inflammation; diabetes; Parkinson's disease or Parkinsonism; severe allergic reactions (including bee stings, food allergies, seasonal allergies, e.g., rhinitis); cancers in which the expression level of adenosine $A_3$ receptor is elevated; and glaucoma.

Preferred methods of the invention include identifying and/or selecting a subject (e.g. mammal, particularly human) that is susceptible to or suffering from a condition disclosed herein, and thereafter administering to the identified and/or selected subject one or more compounds having a tricyclic pyrazolotriazolopyrimidine ring structure of the invention such as a compound of any one of Formulae I through XI, particularly a subject that is identified and/or selected as being susceptible to or suffering from a disease or condition as disclosed herein, including cardiac diseases or disorders including congestive heart failure; neurological disease or injury; sleep disorders, diabetes; various inflammatory diseases and conditions (particularly those inflammatory diseases involving mast cell degranulation); radiation induced fibrosis; liver cirrhosis; asthma; chronic obstructive pulmonary disease; intestinal inflammation; diabetes; Parkinson's disease or Parkinsonism; severe allergic reactions (including bee stings, food allergies, seasonal allergies, e.g., rhinitis); cancers in which the expression level of adenosine $A_3$ receptor is elevated; and glaucoma.

Pharmaceutical compositions also are provided comprising a therapeutically effective amount of one or more compounds having a tricyclic pyrazolotriazolopyrimidine ring structure of the Formulae I though IX as those formulae are defined herein typically together with a pharmaceutically acceptable carrier.

Other aspects of the invention are disclosed infra.

DETAILED DESCRIPTION OF THE INVENTION

As discussed above, we have now found compounds having a tricyclic pyrazolotriazolopyrimidine ring structure useful as allosteric modulators of the family of adenosine receptors, particularly the adenosine $A_1$, $A_{2A}$, $A_{2B}$, and $A_3$ receptors and methods of preparation and use thereof are disclosed. Such compounds may be used to modulate biological responses in the nervous, cardiovascular, respiratory, renal, and immune systems of a mammal, particularly a human. Compounds of the invention are particularly useful for cardiac diseases or disorders including congestive heart failure; neurological disease or injury; sleep disorders, diabetes; various inflammatory diseases and conditions (particularly those inflammatory diseases involving mast cell degranulation); radiation induced fibrosis; liver cirrhosis; asthma; chronic obstructive pulmonary disease; intestinal inflammation; diabetes; Parkinson's disease or Parkinsonism; severe allergic reactions (including bee stings, food allergies, seasonal allergies, e.g., rhinitis); cancers in which the expression level of adenosine $A_3$ receptor is elevated; and glaucoma.

Particularly preferred compounds of the invention include those of the following formula I:

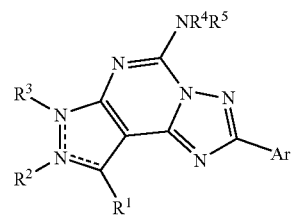

wherein:

Ar is optionally substituted aryl or an optionally substituted heteroalicyclic or heteroaromatic group;

$R^1$ is selected from the group consisting of hydrogen, halogen, cyano, amino, nitro, thio, optionally substituted alkyl, optionally substituted alkenyl, optionally substituted alkynyl, optionally substituted alkoxy, optionally substituted alkylamino, optionally substituted dialkylamino, optionally substituted arylamino, optionally substituted diarylamino, optionally substituted (aryl)(alkyl)amino, optionally substituted alkylthio, optionally substituted alkylsulfinyl, optionally substituted alkylsulfonyl, optionally substituted alkanoyl, optionally substituted carbocyclic aryl, optionally substituted aralkyl, and an optionally substituted heteroalicyclic or heteroaromatic;

$R^2$ and $R^3$ are absent or independently selected from the group consisting of optionally substituted alkyl, optionally substituted alkenyl, optionally substituted alkynyl, optionally substituted aralkyl, optionally substituted alkanoyl, optionally substituted carbocyclic aryl, and an optionally substituted heteroalicyclic or heteroaromatic;

$R^4$ and $R^5$ are independently selected from the group consisting of hydrogen, metabolically cleavable group, optionally substituted alkyl, optionally substituted alkenyl, optionally substituted alkynyl, optionally substituted carbocyclic aryl, optionally substituted alkanoyl, optionally substituted aranoyl, and an optionally substituted heteroalicyclic or heteroaromatic; and pharmaceutically acceptable salt thereof.

Other particularly preferred compounds of the invention include those of the following formula II:

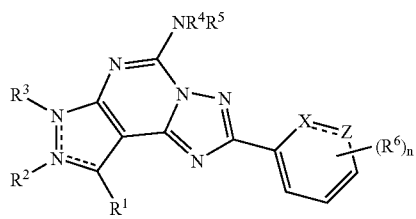

wherein:
X is O, S, N, or $CR^6$;
Z is $CR^6$ when X is either N or $CR^6$, or
Z is absent when X is O or S;
n is an integer of from 1 to about 5;
$R^1$ is selected from the group consisting of hydrogen, halogen, cyano, amino, nitro, thio, optionally substituted alkyl, optionally substituted alkenyl, optionally substituted alkynyl, optionally substituted alkoxy, optionally substituted alkylamino, optionally substituted dialkylamino, optionally substituted arylamino, optionally substituted diarylamino, optionally substituted (aryl)(alkyl)amino, optionally substituted alkylthio, optionally substituted alkylsulfinyl, optionally substituted alkylsulfonyl, optionally substituted alkanoyl, optionally substituted carbocyclic aryl, optionally substituted aralkyl, and an optionally substituted heteroalicyclic or heteroaromatic;
$R^2$ and $R^3$ are absent or independently selected from the group consisting of optionally substituted alkyl, optionally substituted alkenyl, optionally substituted alkynyl, optionally substituted aralkyl, optionally substituted alkanoyl, optionally substituted carbocyclic aryl, and an optionally substituted heteroalicyclic or heteroaromatic;
$R^4$ and $R^5$ are independently selected from the group consisting of hydrogen, metabolically cleavable group, optionally substituted alkyl, optionally substituted alkenyl, optionally substituted alkynyl, optionally substituted carbocyclic aryl, optionally substituted alkanoyl, optionally substituted aranoyl, and an optionally substituted heteroalicyclic or heteroaromatic;
each $R^6$ is independently selected from the group consisting of hydrogen, halogen, cyano, amino, nitro, thio, carboxylate, optionally substituted alkyl, optionally substituted alkenyl, optionally substituted alkynyl, optionally substituted alkoxy, optionally substituted alkylamino, optionally substituted dialkylamino, optionally substituted arylamino, optionally substituted diarylamino, optionally substituted (aryl)(alkyl)amino, optionally substituted alkylthio, optionally substituted alkylsulfinyl, optionally substituted alkylsulfonyl, optionally substituted alkanoyl, optionally substituted carbocyclic aryl, optionally substituted aralkyl, optionally substituted carboxamide, optionally substituted carboxy aralkyl, optionally substituted benzoate, and an optionally substituted heteroalicyclic or heteroaromatic; and pharmaceutically acceptable salt thereof.

The invention also provides particularly preferred compounds including those of the following formula III:

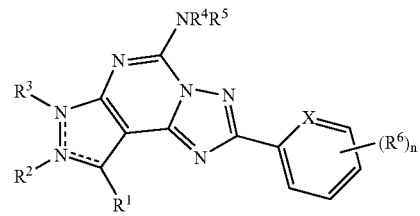

wherein
X is N or $CR^6$;
n is an integer of from 1 to about 5;
$R^1$ is selected from the group consisting of hydrogen, halogen, cyano, amino, nitro, thio, optionally substituted alkyl, optionally substituted alkenyl, optionally substituted alkynyl, optionally substituted alkoxy, optionally substituted alkylamino, optionally substituted dialkylamino, optionally substituted arylamino, optionally substituted diarylamino, optionally substituted (aryl)(alkyl)amino, optionally substituted alkylthio, optionally substituted alkylsulfinyl, optionally substituted alkylsulfonyl, optionally substituted alkanoyl, and optionally substituted aralkyl;
$R^2$ and $R^3$ are absent or independently selected from the group consisting of optionally substituted alkyl, optionally substituted alkenyl, optionally substituted alkynyl, optionally substituted aralkyl, optionally substituted alkanoyl, optionally substituted carbocyclic aryl, and an optionally substituted heteroalicyclic or heteroaromatic;
$R^4$ and $R^5$ are independently selected from the group consisting of hydrogen, metabolically cleavable group, optionally substituted alkyl, optionally substituted alkenyl, optionally substituted alkynyl, optionally substituted carbocyclic aryl, optionally substituted alkanoyl, optionally substituted aranoyl, or an optionally substituted heteroalicyclic and heteroaromatic;
each $R^6$ is independently selected from the group consisting of hydrogen, halogen, cyano, amino, thio, carboxylate, optionally substituted alkyl, optionally substituted alkenyl, optionally substituted alkynyl, optionally substituted alkoxy, optionally substituted alkylamino, optionally substituted dialkylamino, optionally substituted alkylthio, optionally substituted alkylsulfinyl, optionally substituted alkylsulfonyl, optionally substituted alkanoyl, optionally substituted carboxamide, optionally substituted carboxy aralkyl, and optionally substituted benzoate; and pharmaceutically acceptable salt thereof.

Preferred compounds of Formula III include those compounds according to the following Formula IV:

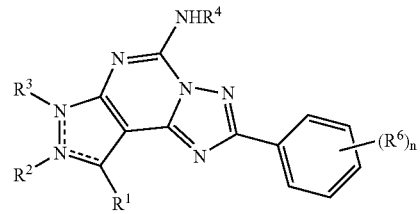

wherein n is an integer of from 1 to about 3;

R¹ is selected from the group consisting of hydrogen, halogen, cyano, amino, nitro, thio, optionally substituted $C_{1-6}$alkyl, optionally substituted $C_{1-6}$alkoxy, optionally substituted $C_{1-6}$alkylamino, optionally substituted di($C_{1-6}$alkyl)amino, optionally substituted arylamino, optionally substituted $C_{1-6}$alkylthio, optionally substituted $C_{2-12}$alkanoyl, and optionally substituted $C_{7-15}$aralkyl;

R² and R³ are absent or independently selected from the group consisting of optionally substituted $C_{1-6}$alkyl, optionally substituted $C_{2-6}$alkenyl, optionally substituted $C_{2-6}$alkynyl, optionally substituted $C_{7-15}$aralkyl, optionally substituted $C_{2-6}$alkanoyl;

R⁴ is independently selected from the group consisting of hydrogen, metabolically cleavable group, optionally substituted $C_{1-6}$alkyl, optionally substituted phenyl, optionally substituted $C_{2-6}$alkanoyl, and optionally substituted $C_{7-15}$aranoyl;

each R⁶ is independently selected from the group consisting of hydrogen, halogen, cyano, amino, thio, carboxylate, optionally substituted $C_{1-6}$alkyl, optionally substituted $C_{1-6}$alkoxy, optionally substituted $C_{1-6}$alkylamino, optionally substituted di($C_{1-6}$alkyl)amino, optionally substituted $C_{1-6}$alkylthio, optionally substituted $C_{1-6}$alkanoyl, optionally substituted carboxamide, optionally substituted carboxy aralkyl, and optionally substituted benzoate; and pharmaceutically acceptable salt thereof.

Other preferred compounds of Formula III include those compounds according to the following Formula V:

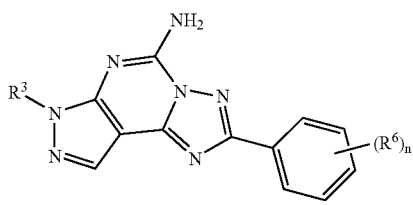

wherein n is an integer of from 1 to about 3;

R³ are absent or independently selected from the group consisting of optionally substituted $C_{1-6}$alkyl, optionally substituted $C_{2-6}$alkenyl, optionally substituted $C_{2-6}$alkynyl, optionally substituted $C_{7-15}$aralkyl, optionally substituted $C_{2-6}$alkanoyl;

each R⁶ is independently selected from the group consisting of hydrogen, halogen, cyano, amino, thio, carboxylate, optionally substituted $C_{1-6}$alkyl, optionally substituted $C_{1-6}$alkoxy, optionally substituted $C_{1-6}$alkylamino, optionally substituted di($C_{1-6}$alkyl)amino, optionally substituted $C_{1-6}$alkylthio, optionally substituted $C_{1-6}$alkanoyl, optionally substituted carboxamide, optionally substituted carboxy aralkyl, and optionally substituted benzoate; and pharmaceutically acceptable salt thereof.

Particularly preferred compounds of any one of Formula III, IV, or V include those compounds in which R³ is a aryl-($C_{1-6}$)alkylene group.

Particularly preferred compounds of the invention include those of the following formula VI:

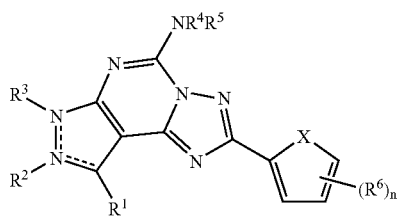

wherein:

X is O or S;

n is an integer of from 1 to about 3;

R¹ is selected from the group consisting of hydrogen, halogen, cyano, amino, nitro, thio, optionally substituted alkyl, optionally substituted alkenyl, optionally substituted alkynyl, optionally substituted alkoxy, optionally substituted alkylamino, optionally substituted dialkylamino, optionally substituted arylamino, optionally substituted diarylamino, optionally substituted (aryl)(alkyl)amino, optionally substituted alkylthio, optionally substituted alkylsulfinyl, optionally substituted alkylsulfonyl, optionally substituted alkanoyl, optionally substituted carbocyclic aryl, optionally substituted aralkyl, and an optionally substituted heteroalicyclic or heteroaromatic;

R² and R³ are absent or independently selected from the group consisting of optionally substituted alkyl, optionally substituted alkenyl, optionally substituted alkynyl, optionally substituted aralkyl, optionally substituted alkanoyl, optionally substituted carbocyclic aryl, and an optionally substituted heteroalicyclic or heteroaromatic;

R⁴ and R⁵ are independently selected from the group consisting of hydrogen, metabolically cleavable group, optionally substituted alkyl, optionally substituted alkenyl, optionally substituted alkynyl, optionally substituted carbocyclic aryl, optionally substituted alkanoyl, optionally substituted aranoyl, and an optionally substituted heteroalicyclic or heteroaromatic;

each R⁶ is independently selected from the group consisting of hydrogen, halogen, cyano, amino, nitro, thio, carboxylate, optionally substituted alkyl, optionally substituted alkenyl, optionally substituted alkynyl, optionally substituted alkoxy, optionally substituted alkylamino, optionally substituted dialkylamino, optionally substituted arylamino, optionally substituted diarylamino, optionally substituted (aryl)(alkyl)amino, optionally substituted alkylthio, optionally substituted alkylsulfinyl, optionally substituted alkylsulfonyl, optionally substituted alkanoyl, optionally substituted carbocyclic aryl, optionally substituted aralkyl, optionally substituted carboxamide, optionally substituted carboxy aralkyl, optionally substituted benzoate, and an optionally substituted heteroalicyclic or heteroaromatic; and pharmaceutically acceptable salt thereof.

Particularly preferred compounds of the invention according to Formula VI include those compounds wherein X is O, e.g., those compounds having a furanyl group at the 2-position of the tricyclic pyrazolotriazolopyrimidine ring structure.

Preferred compounds of Formula VI include those compounds according to the following formula VII:

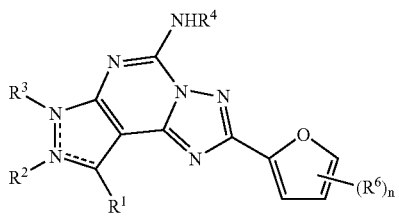

wherein:

n is an integer of from 1 to about 3;

$R^1$ is selected from the group consisting of hydrogen, amino, thio, optionally substituted alkyl, optionally substituted alkoxy, optionally substituted alkylamino, optionally substituted dialkylamino, optionally substituted arylamino, optionally substituted alkylthio, optionally substituted alkanoyl, and optionally substituted aralkyl;

$R^2$ is absent or selected from optionally substituted alkyl and optionally substituted aralkyl;

$R^3$ is absent or selected from the group consisting of optionally substituted alkyl, optionally substituted aralkyl, and optionally substituted alkanoyl;

$R^4$ is selected from the group consisting of hydrogen, metabolically cleavable group, optionally substituted alkyl, optionally substituted alkanoyl, optionally substituted carboxy aralkyl, and optionally substituted N-aryl-carboxamide;

each $R^6$ is independently selected from the group consisting of hydrogen, halogen, cyano, amino, nitro, thio, carboxylate, optionally substituted alkyl, optionally substituted alkoxy, optionally substituted alkylamino, optionally substituted dialkylamino, optionally substituted arylamino, optionally substituted diarylamino, optionally substituted (aryl)(alkyl)amino, optionally substituted alkylthio, optionally substituted alkylsulfinyl, optionally substituted alkylsulfonyl, optionally substituted alkanoyl, optionally substituted carbocyclic aryl, optionally substituted aralkyl, optionally substituted carboxamide, optionally substituted carboxy aralkyl, optionally substituted benzoate, and an optionally substituted heteroalicyclic or heteroaromatic; and pharmaceutically acceptable salt thereof.

Additional preferred compounds of Formula VI include those compounds according to the following formula VIII:

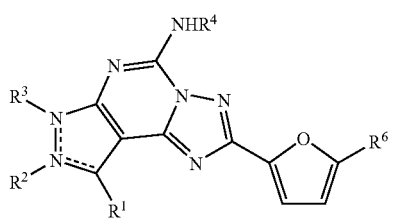

wherein:

$R^1$ is selected from the group consisting of hydrogen, amino, thio, optionally substituted $C_{1-6}$alkyl, optionally substituted $C_{1-6}$alkoxy, optionally substituted $C_{1-6}$ alkylamino, optionally substituted di($C_{1-6}$)alkylamino, optionally substituted phenylamino which may be substituted with up to three groups selected from halogen, $C_{1-6}$alkyl, $C_{1-6}$alkoxy, and hydroxy, optionally substituted $C_{1-6}$alkylthio, optionally substituted $C_{1-6}$alkanoyl, and optionally substituted $C_{7-12}$aralkyl;

$R^2$ is absent or selected from optionally substituted $C_{1-6}$alkyl and optionally substituted $C_{7-12}$aralkyl;

$R^3$ is absent or selected from the group consisting of optionally substituted a $C_{1-6}$alkyl, optionally substituted $C_{7-12}$aralkyl, and optionally substituted $C_{2-6}$alkanoyl;

$R^4$ is selected from the group consisting of hydrogen, metabolically cleavable group, optionally substituted $C_{1-6}$alkyl, optionally substituted $C_{2-6}$alkanoyl, optionally substituted $C_{8-12}$alkyl carboxy aralkyl, and optionally substituted N-phenyl-carboxamide;

$R^6$ is independently selected from the group consisting of hydrogen, halogen, cyano, amino, nitro, thio, carboxylate, optionally substituted $C_{1-6}$alkyl, optionally substituted $C_{1-6}$alkoxy, optionally substituted $C_{1-6}$alkyl amino, optionally substituted di($C_{1-6}$)alkyl amino, optionally substituted $C_{1-6}$alkylthio, optionally substituted $C_{2-6}$alkanoyl, optionally substituted piperazine or optionally substituted morpoline; and pharmaceutically acceptable salt thereof.

Other preferred compounds of the invention include those of the following formulae:

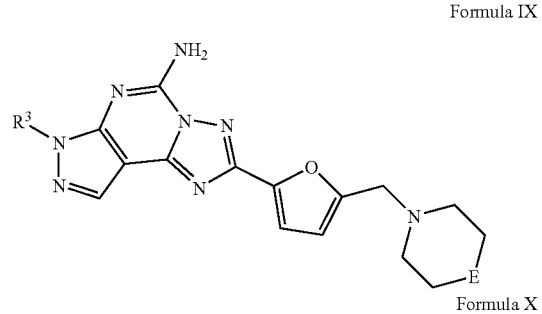

Formula IX

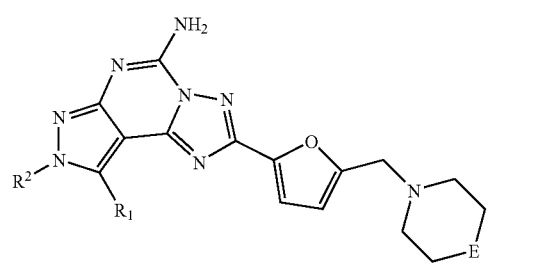

Formula X wherein:

$R^1$ is selected from the group consisting of hydrogen, $C_{1-6}$alkylamino, di($C_{1-6}$)alkylamino, and $C_{1-6}$alkylthio;

$R^2$ is selected from optionally substituted $C_{1-6}$alkyl and optionally substituted $C_{7-12}$aralkyl;

$R^3$ is selected from the group consisting of optionally substituted a $C_{1-6}$alkyl, optionally substituted $C_{7-12}$aralkyl, and optionally substituted $C_{2-6}$alkanoyl;

E is O or N—$C_{1-6}$alkyl; and pharmaceutically acceptable salt thereof.

Other preferred compounds of Formula VI include those compounds according to the following formula XI:

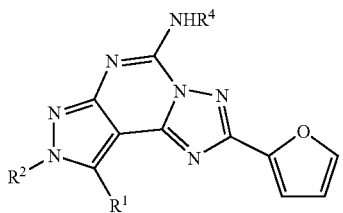

Formula XI wherein $R^1$ is $C_{1-6}$alkyl amino, anilido which may be optionally substituted with 0, 1, 2, or 3 groups selected from halogen, $C_{1-6}$alkyl, $C_{1-6}$alkoxy, hydroxy or amino, $C_{1-6}$alkylthio, piperazine or N—$C_{1-6}$alkyl-piperazine;

$R^2$ is $C_{1-6}$alkyl or phenyl-$C_{1-4}$alkylene;

$R^4$ is hydrogen, or $R^4$ is C(O)NH-phenyl, C(O)CH$_2$-phenyl which may be optionally substituted with 0–3 groups selected from $C_{1-6}$alkyl, $C_{1-6}$alkoxy, hydroxy or $C_{1-2}$alkylenedioxy; and pharmaceutically acceptable salts thereof.

Specifically preferred compounds of the invention include the following and pharmaceutically acceptable salts of such compounds:

4-(5-Amino-7-phenethyl-7H-pyrazolo[4,3-e][1,2,4]triazolo[1,5-c]pyrimidin-2-yl)-phenol;

2-(4-Chloro-phenyl)-7-phenethyl-7H-pyrazolo[4,3-e][1,2,4]triazolo[1,5-c]pyrimidin-5-ylamine;

2-(2-Ethoxy-phenyl)-7-phenethyl-7H-pyrazolo[4,3-e][1,2,4]triazolo[1,5-c]pyrimidin-5-ylamine;

[4-(5-Amino-7-phenethyl-7H-pyrazolo[4,3-e][1,2,4]triazolo[1,5-c]pyrimidin-2-yl)-phenoxy]-acetic acid ethyl ester;

[4-(5-Amino-7-phenethyl-7H-pyrazolo[4,3-e][1,2,4]triazolo[1,5-c]pyrimidin-2-yl)-phenoxy]-acetic acid;

2-[4-(5-Amino-7-phenethyl-7H-pyrazolo[4,3-e][1,2,4]triazolo[1,5-c]pyrimidin-2-yl)-phenoxy]-N-(4-iodo-phenyl)-acetamide;

N9-Ethyl-2-furan-2-yl-8-methyl-8H-pyrazolo[4,3-e][1,2,4]triazolo[1,5-c]pyrimidiine-5,9-diamine;

N9-Ethyl-2-furan-2-yl-8-methyl-8H-pyrazolo[4,3-e][1,2,4]triazolo[1,5-c]pyrimidine-5,9-diamine hydrochloride salt;

2-Furan-2-yl-N9-(4-methoxy-phenyl)-8-methyl-8H-pyrazolo[4,3-e][1,2,4]triazolo[1,5-c]pyrimidine-5,9-diamine;

2-Furan-2-yl-8-methyl-9-(4-methyl-piperazin-1-yl)-8H-pyrazolo[4,3-e][1,2,4]triazolo[1,5-c]pyrimidin-5-ylamine;

2-Furan-2-yl-8-methyl-9-(4-methyl-piperazin-1-yl)-8H-pyrazolo[4,3-e][1,2,4]triazolo[1,5-c]pyrimidin-5-ylamine dihydrochloride salt;

2-Furan-2-yl-8-methyl-9-methylsulfanyl-8H-pyrazolo[4,3-e][1,2,4]triazolo[1,5-c]pyrimidin-5-ylamine;

2-Furan-2-yl-8-methyl-9-propylsulfanyl-8H-pyrazolo[4,3-e][1,2,4]triazolo[1,5-c]pyrimidin-5-ylamine;

2-Furan-2-yl-9-methylsulfanyl-8-(3-phenyl-propyl)-8H-pyrazolo[4,3-e][1,2,4]triazolo[1,5-c]pyrimidin-5-ylamine;

1-(9-Ethylamino-2-furan-2-yl-8-methyl-8H-pyrazolo[4,3-e][1,2,4]triazolo[1,5-c]pyrimidin-5-yl)-3-(4-methoxy-phenyl)-urea;

1-(9-Ethylamino-2-furan-2-yl-8-methyl-8H-pyrazolo[4,3-e][1,2,4]triazolo[1,5-c]pyrimidin-5-yl)-3-(4-methoxy-phenyl)-urea hydrochloride salt;

1-[2-Furan-2-yl-8-methyl-9-(4-methyl-piperazin-1-yl)-8H-pyrazolo[4,3-e][1,2,4]triazolo[1,5-c]pyrimidin-5-yl]-3-(4-methoxy-phenyl)-urea;

1-(2-Furan-2-yl-8-methyl-9-methylsulfanyl-8H-pyrazolo[4,3-e][1,2,4]triazolo[1,5-c]pyrimidin-5-yl)-3-(4-methoxy-phenyl)-urea;

N-(2-Furan-2-yl-8-methyl-9-methylsulfanyl-8H-pyrazolo[4,3-e][1,2,4]triazolo[1,5-c]pyrimidin-5-yl)-2-(4-methoxy-phenyl)-acetamide;

N-(2-Furan-2-yl-8-methyl-9-methylsulfanyl-8H-pyrazolo[4,3-e][1,2,4]triazolo[1,5-c]pyrimidin-5-yl)-2-(4-isobutyl-phenyl)-acetamide;

2-Benzo[1,3]dioxol-5-yl-N-(2-furan-2-yl-8-methyl-9-methylsulfanyl-8H-pyrazolo[4,3-e][1,2,4]triazolo[1,5-c]pyrimidin-5-yl)-acetamide;

2-Benzo[1,3]dioxol-5-yl-N-(9-ethylamino-2-furan-2-yl-8-methyl-8H-pyrazolo[4,3-e][1,2,4]triazolo[1,5-c]pyrimidin-5-yl)-acetamide;

4-(5-Amino-2-furan-2-yl-8-methyl-8H-pyrazolo[4,3-e][1,2,4]triazolo[1,5-c]pyrimidin-9-ylamino)-phenol;

8-Methyl-2-[5-(4-methyl-piperazin-1-ylmethyl)-furan-2-yl]-9-methylsulfanyl-8H-pyrazolo[4,3-e][1,2,4]triazolo[1,5-c]pyrimidin-5-ylamine;

8-Methyl-9-methylsulfanyl-2-(5-morpholin-4-ylmethyl-furan-2-yl)-8H-pyrazolo[4,3-e][1,2,4]triazolo[1,5-c]pyrimidin-5-ylamine; or a pharmaceutically acceptable salt thereof.

As used herein, the term "alkyl" refers to monovalent straight, branched, or cyclic alkyl groups preferably having from 1 to 20 carbon atoms, more preferably 1 to 10 carbon atoms, and most preferably 1 to 6 carbon atoms ("lower alkyl"). This term is exemplified by groups such as methyl, ethyl, n-propyl, iso-propyl, n-butyl, iso-butyl, n-hexyl, 2-methylpropyl, 3-methylbutyl, and the like. The terms "alkylene" and "lower alkylene" refer to divalent radicals of the corresponding alkane. Further, as used herein, other moieties having names derived from alkanes, such as alkoxy, alkanoyl, alkenyl, cycloalkenyl, etc., when modified by "lower," have carbon chains of ten or fewer carbon atoms. In those cases where the minimum number of carbons required are greater than one, e.g., alkenyl and alkynyl (minimum of two carbons) and cycloalkyl (minimum of three carbon atoms), it is to be understood that the term "lower" means at least the minimum number of carbon atoms.

As indicated above, alkyl groups may be substituted e.g., by having from 1 to 5 substituents, and preferably from 1 to 3 substituents, suitably selected from the group consisting of alkoxy, substituted alkoxy, cycloalkoxy, substituted cycloalkoxy, cycloalkyl, substituted cycloalkyl, cycloalkenyl, substituted cycloalkenyl, alkynyl, substituted alkynyl, acyl, amino, aryl, substituted aryl, carboxyl, carboxyalkyl, cyano, fluoro, hydroxyl, halogen, heteroaryl, heterocyclic, nitro, alkylthio, thiol, mono(alkyl)-amino, di(alkyl)amino, mono(substituted alkyl)amino, di(substituted alkyl)amino, unsymmetric disubtituted amines having different substitutents selected from alkyl, substituted alkyl, aryl, substituted aryl, aralkyl, and substituted aralkyl, —SO-alkyl, —SO-substituted alkyl, —SO-aryl, —SO-substituted aryl, —SO$_2$-alkyl, —SO$_2$-substituted alkyl, —SO$_2$-aryl, and —SO$_2$-substituted aryl. As used herein, other moieties having the prefix "substituted" are intended to include one or more of the substituents listed above.

As used herein, the term "alkenyl" refers to straight or branched alkenyl groups having from 2 to 20, more preferably from 2 to 10 carbon atoms, and most preferably 2 to 6 carbons atoms, and having at least 1 and preferable from 1 to 3 sites of alkenyl unsaturation. This term is exemplified by groups such as ethenyl (CH=CH$_2$), 1-propenyl (CH=CH—CH$_3$), 2-propenyl (C(CH$_3$)=CH$_2$), 3-methyl-2-pentenyl (CH$_2$—CH=C(CH$_3$)—CH$_2$CH$_3$), and the like.

As used herein, the term "alkynyl" refers to straight or branched alkynyl groups having from 2 to 20 carbon atoms, more preferably from 2 to 10 carbon atoms, and most preferably from 2 to 6 carbon atoms, and having at least 1 and preferably from 1 to 2 sites of alkynyl unsaturation. This term is exemplified by groups such as ethynyl, 1-propynyl, 2-propynyl, 2-butynyl, 4,4-dimethyl-2-pentynyl, and the like.

As used herein, the term "cycloalkyl" refers to cyclic alkyl groups of from 3 to 20 carbon atoms having a single cyclic ring or multiple rings joined in either a fused or spirocyclic condensation. This term is exemplified by groups such as cyclopropyl, cyclopentyl, cyclohexyl, cyclooctyl, norbornyl, perhydrofluorenyl, adamantyl, and the like. As indicated, the term alkyl is inclusive of cycloalkyl unless otherwise indicated.

As used herein, the term "cycloalkenyl" refers to cyclic alkenyl groups of from 5 to 20 carbon atoms having a single cyclic ring or multiple rings joined in either a fused or spirocyclic condensation and having at least 1 and preferably from 1 to 2 sites of alkenyl unsaturation. This term is exemplified by groups such as cyclopentenyl, cycloheptenyl, 1,3-cyclooctadienyl, cycloheptatrienyl, bicyclo[2.2.1]hepta-2,5-dienyl, and the like.

The term "carbon alicyclic group" refers to structures where each ring member is carbon and the group is non-aromatic, although the group may have one or more endocyclic carbon-carbon double bonds. Preferred carbon alicyclic groups have 5, 6, 7 or 8 ring atoms, more preferred 5, 6 or 7 ring atoms.

As used herein, the term "aryl" or "carbocyclic aryl" refers to an unsaturated, aromatic, carbocyclic group of from 6 to 20 carbon atoms having a single ring or multiple condensed rings. This term is exemplified by groups such as phenyl, 1-naphthyl, 2-naphthyl, anthracenyl, 1,2-benzanthracenyl, and the like. As used herein, the term "aryl" also refers to those fused-ring hydrocarbons in which the aromatic ring or rings are condensed to additional non-aromatic rings. In this manner, this term is exemplified by groups such as fluorenyl, acenaphthenyl, biphenylenyl, fluoranthenyl, and the like. Unless otherwise constrained by the definition for the aryl substituent, such aryl groups can optionally be substituted with from one to five substituents, preferably one to three substituents, selected from the list given herein.

As used herein, the term "aralkyl" refers to an aryl or substituted aryl group, attached to an alkylene group or substituted alkylene group, where aryl, substituted aryl, alkylene, and substituted alkylene are as defined herein.

As used herein, the term "heteroalicyclic" refers to a monovalent saturated or unsaturated carbocyclic group having a single ring or multiple condensed rings, from 1 to 15 carbon atoms and from 1 to 5 heteroatoms within the ring or rings, preferably from 1 to 9 carbon atoms and from 1 to 4 heteroatoms within the ring or rings, selected from the group of heteroatoms consisting of nitrogen, sulfur, and oxygen. This term is exemplified by groups such as tetrahydrofuranyl, pyrrolinyl, pyrrolidinyl, oxazolidinyl, thiazolidinyl, imidazolinyl, imidazolidinyl, piperidinyl, piperazinyl, quinuclidinyl, thiomorpholinyl, morpholinyl, dioxolanyl, and the like.

As used herein, the term "heteroaromatic" refers to a 5-membered or 6-membered heterocyclic, aromatic group, which can optionally be fused to an aryl or substituted aryl ring, where heterocyclic, aryl, and substituted aryl are as defined herein. This term is exemplified by groups such as pyrrolyl, furanyl, thiophenyl, pyrazolyl, imidazolyl, isoxazolyl, oxazolyl, isothiazolyl, thiazolyl, thiadiazolyl, triazolyl, tetrazolyl, pyridyl, pyridazyl, pyrimidyl, indolyl, benzofuranyl, benzotriazolyl, quinolinyl, isoquinolinyl, and the like. Optionally, the heteroaryl group may be fused to a second or third heteroaryl group. In this context, this term is exemplified by groups such as 1,2,3-triazolo[4,5-B]pyridinyl, s-triazolo[1,5-A]pyrimidinyl, pyrazolo[3,4-D]pyrimidinyl, purinyl, pterinyl, pteridinyl, pyrimido[5,4-D]pyrimidinyl, and the like.

As used herein, the term "alkanoyl" refers to the groups alkyl-C(O)—, substituted alkyl-C(O), cycloalkyl-C(O), substituted cycloalkyl-C(O), aryl-C(O), substituted aryl-C(O), heterocyclic-C(O), and heteroaryl-C(O), where alkyl, substituted alkyl, cycloalkyl, substituted cycloalkyl, aryl, substituted aryl, heterocyclic, and heteroaryl are as defined herein.

As used herein, the term "alkoxy" refers to the group "alkyl-O—", "substituted alkyl-O—", "cycloalkyl-O—", or "substituted cycloalkyl-O—" where alkyl, substituted alkyl, cycloalkyl, and substituted cycloalkyl are as defined herein. This term is exemplified by such groups as methoxy, ethoxy, 1-propoxy, 2-propoxy, 1-butyloxy, tert-butyloxy, cyclopentyloxy, cyclohexylethoxy, and the like.

As used herein, the term "halo" or "halogen" refers to fluoro, chloro, bromo, and iodo groups.

Heteroalkylene groups typically will have about 1 to about 8 atoms in the chain, more typically 1 to about 6 atoms in the linkage and at least one hetero atom (N, O or S) as a divalent chain member. As the terms "heteroalkylene" and "alkylene" are used herein, such chains may have one or more double or triple bonds in the chain, i.e. the term heteroalkylene is inclusive of heteroalkenylene and heteroalkynylene groups, and the term alkylene is inclusive of heteroalkenylene and heteroalkynylene groups.

Alkylthio groups of compounds of the invention suitably having one or more thioether linkages, typically 1, 2 or 3 thioether linkages, and preferably 1 to about 1'2 carbon atoms, more preferably 1 to about 6 carbon atoms.

Alkylsulfinyl groups of compounds of the invention suitably having one or more sulfinyl (SO) groups, typically 1, 2 or 3 sulfinyl linkages, and preferably 1 to about 1'2 carbon atoms, more preferably 1 to about 6 carbon atoms.

Alkylsulfonyl groups of compounds of the invention suitably having one or more sulfonyl (SO$_2$) groups, typically 1, 2 or 3 SO$_2$ linkages, and preferably 1 to about 1'2 carbon atoms, more preferably 1 to about 6 carbon atoms.

Preferred alkylamino groups of compounds of the invention include those that have one or more primary, secondary and/or tertiary amine groups, preferably 1, 2 or 3 total amine groups, and from 1 to about 12 carbon atoms, more preferably 1 to about 6 carbon atoms.

The term "metabolically cleavable group" as used herein denotes a group which can be cleaved in vivo upon administration to a subject, particularly to provide a primary amine. Examples of metabolically cleavable groups include optionally substituted C$_{1-8}$ alkyl such as methyl, acetyl and other alkanoyl preferably optionally substituted C$_{1-6}$ alkanoyl, ethoxycarbonyl, benzoyl, alkoxymethyl, lactates, sugar groups, and the like.

As indicated, various substituents compounds of the invention including compounds of Formulae I through XI may be optionally substituted. Suitable group that may be present on a "substituted" substituent include halogen (F, Cl, Br or I); cyano; hydroxyl; nitro; alkaonyl e.g. C$_{1-6}$alkanoyl group such as acetyl and the like; alkyl groups e.g. $C_{1-6}$alkyl; alkoxy groups e.g. $C_{1-6}$alkoxy; alkylsulfinyl such as groups having 1 to about 6 carbon atoms; alkylsulfonyl such as groups having 1 to about 6 carbon atoms; alkylamino such as groups having 1 to about 6 carbon atoms; carbocyclic aryl such as phenyl and naphthyl; heteroalicyclic such as those discussed above; or heteromatic typically having 1, 2 or 3 N, O or S ring atoms. A "substituted" substituent of a compound of the invention may be substituted at one or more available positions, typically 1, 2 or 3 positions, by one or more suitable groups such as those listed immediately above.

As to any of the above groups that contain one or more substituents, it is understood by those skilled in the art, that such groups do not contain any substitution or substitution patterns which are sterically unfeasible and or synthetically impracticable.

The invention provides new molecules which possess a core ring structure derived from the lead compounds SCH 58261 and MRE and novel ring position substitution patterns. We introduced structural variability in the substituents at the 2, 5, 7, 8, and 9 positions of the pyrazolotriazolopyrimidine ring structure in order to evaluate the change in binding affinity to various adenosine receptors and to measure binding selectivity for a specific adenosine receptor subtype. The compounds provided by the instant invention also provide a better understanding of the important features about the associated structure-activity relationships (SAR).

We investigated the effect of varying the substituent at two positions of the tricyclic pyrazolotriazolopyrimidine structure: the 2 and the 9 position. For all the $A_{2A}$ adenosine receptor antagonists, the furanyl group in the 2 position was shown to be important for the binding activity of the molecule. Substitution of this heterocycle with other heterocyclic rings, e.g. thiophene or tetrahydrofuranyl led to a severe loss of affinity of the compound for the relavent adenosine receptor. We tried to introduce in the same position an aromatic ring substituted in the para position with different groups (e.g. halogens, free hydroxyl group, amide, and free carboxylic acid functions) to create a more favorable electronic condition for interaction with the adenosine receptor. The ortho position of the aromatic ring was also functionalized with an alkoxy group, e.g., an ethoxy group to imitate the 2'-oxo residue of the furan-2-yl ring. The remaining part of the structure of this new class of compounds synthesized was maintained as in the lead compound SCH 58261 in order to appreciate and evaluate the change in receptor affinity and selectivity. The general structure of the class of compounds of the invention modified in 2 position of the tricyclic pyrazolotriazolopyrimidine ring structure are depicted in the following structures:

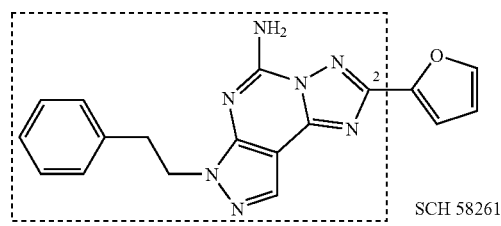

SCH 58261

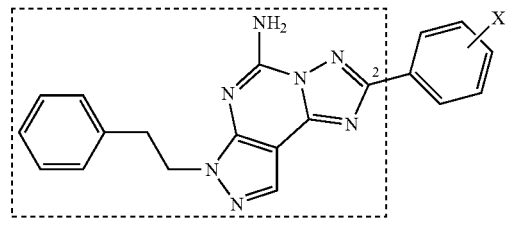

X = 4-OH, 4-Cl, 2-OEt, 4-OCH$_2$CO$_2$Et,
4-OCH$_2$CO$_2$H, 4-OCH$_2$CONHPh-p-I

The present invention has also provides compounds having a pyrazolotriazolopyrimidine ring structure which is substituted at the 9 position in order to evaluate the changing in terms of binding affinity and receptor selectivity for binding to $A_{2A}$ or $A_3$ adenosine receptor subtypes. We were able to compare the binding activity and selectivity of the compounds of the invention with the lead compounds, SCH and MRE.

Compounds of the invention having a $C^9$ substitutent typically are also $N^8$-substituted. Preferable $N^8$-substituted groups include alkyl groups, preferably small alkyl groups such as $C_{1-6}$alkyl groups including methyl or ethyl, and aralkyl groups such as phenyl-$C_{1-6}$alkylene groups. All substituents introduced at the 9-position have different parameters of steric hindrance and different hydrophylic/lipophylic balance relationships: they are, in fact, cycloalkyl, alkyl or amine functional groups with are coupled to the tricyclic pyrazolotriazolopyrimidine ring structure through a thioether linkage or an amine linkage. Preferred specific embodiments of the invention having $C^9$-substitution are provided in Table 1.

TABLE 1

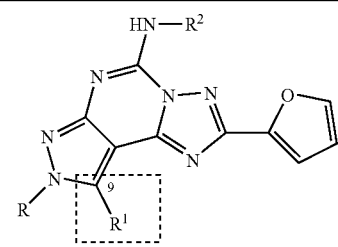

| Compound | R | R$^1$ | R$^2$ |
|---|---|---|---|
| 38 | CH$_3$ | NHCH$_2$CH$_3$ | H |
| 39 | CH$_3$ | NHPh-p-OMe | H |
| 40 | CH$_3$ | N-Me-piperazine | H |
| 41 | CH$_3$ | SCH$_3$ | H |
| 42 | CH$_3$ | S(CH$_2$)$_2$CH$_3$ | H |
| 43 | Ph(CH$_2$)$_3$ | SCH$_3$ | H |
| 44 | CH$_3$ | NHCH$_2$CH$_3$ | CONHPh-p-OMe |
| 45 | CH$_3$ | N-Me-piperazine | CONHPh-p-OMe |
| 46 | CH$_3$ | SCH$_3$ | CONHPh-p-OMe |
| 47 | CH$_3$ | SCH$_3$ | COCH$_2$Ph-p-OMe |
| 48 | CH$_3$ | SCH$_3$ | COCH$_2$Ph-p-isobutyl |
| 49 | CH$_3$ | SCH$_3$ | COCH$_2$Ph-3,4-Medioxy |
| 50 | CH$_3$ | NHCH$_2$CH$_3$ | COCH$_2$Ph-3,4-Medioxy |
| 52 | CH$_3$ | NH-Ph-p-OH | H |
| 53 | CH$_3$ | NHCH$_2$CH$_3$•HCl | H |
| 54 | CH$_3$ | N-Me-piperazine•2HCl | H |
| 55 | CH$_3$ | NHCH$_2$CH$_3$•HCl | CONHPhp-OMe |

Compounds of the invention were tested by binding assays against each of the four different types of adenosine receptors with particular attention to the results obtained from the interaction with $A_{2A}$ and $A_3$ receptor subtypes.

All the compounds previously reported having a tricyclic pyrazolotriazolopyrimidine ring structure and possessing adenosine antagonist activity are very lipophilic, which presented significant problems for several biological tests. Applicants have surprisingly discovered that a hydrophilic functional group may be introduced at the 5 position of the 2-furanyl group via a Mannich reaction. Introduction of hydrophilic groups onto compounds of the invention improves the water solubility of the compounds of the invention so modified and facilitates the evaluation of binding affinity and binding selectivity of the compounds provided by the instant amendment. The amines used for this type of reaction were morpholine and N-methylpiperazine suitably protonated by treatment with hydrochloric acid solution in order to increase the solubility and to make easy the pharmacological testing.

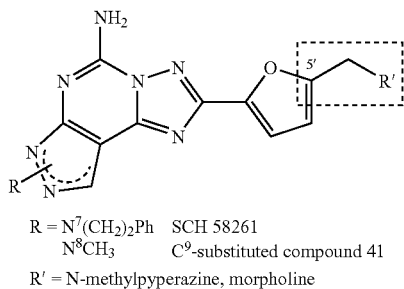

R = $N^7(CH_2)_2Ph$  SCH 58261
$N^8CH_3$    $C^9$-substituted compound 41

R' = N-methylpyperazine, morpholine

Chemistry

The general synthesis of 2-aryl-pyrazolo-triazolo-pyrimidines is reported in the Scheme 1.

The synthetic steps for the synthesis of this new class of compounds are the same utilized for the synthesis of SCH 58261 and analogues (according to Gatta et al.)[16], except for the substituted hydrazide utilized. The 4-cyano-5-amino-1-(2-phenylethyl)pyrazole[15] 1 was transformed into the corresponding imidate 2 by refluxing in triethylorthoformate. The imidate was reacted with 4-hydroxybenzoic acid hydrazide, 4-chlorobenzoic acid hydrazide, 2-ethoxybenzoic acid hydrazide in refluxing 2-methoxyethanol to provide the pyrazolo[4,3-e]pyrimidine intermediates. The latter compounds were converted through a thermally induced cyclization in diphenylether to the derivatives 3a–c in a good yield.

Treatment of 3a–c with dilute hydrochloric acid induce pyrimidine ring opening to furnish the amines 4a–c in quantitative yield. These derivatives were converted into the final compounds 5a–c by reaction with an excess of cyanamide in 1-methyl-2-pyrrolidone at 140° C.

The tricyclic compound 5a was functionalized at the hydroxy group by treatment with 2-chloroacetylchloride or 2-chloro-N-(4-iodophenyl)acetamide in DMF as solvent in order to obtain the derivatives 6 and 8. And finally, the derivative 6 was converted into 7 by treatment with aqueous HCl in dioxane.

The hydrolysis and the acylations reactions used to form compounds 6, 7, and 8 are provided in Schemes 2 and 3.

The synthesis of pyrazolo[4,3-e]-1,2,4-triazolo[1,5-c]pyrimidine derivatives substituted in 9 position is reported in Schemes 4, 5, 6, 7.

The reaction between malononitrile, carbondisulfide and methyl iodide, commercially available, in the presence of $K_2CO_3$ as a base and DMF as a solvent, gave the 2-(bis-methylsulfanilmethylene)malononitrile 9 that, by reaction with methylhydrazine or 3-phenylpropylhydrazine in ethanol as a solvent, gave the amino cyano pyrazoles 14 and 15 (Scheme 5).

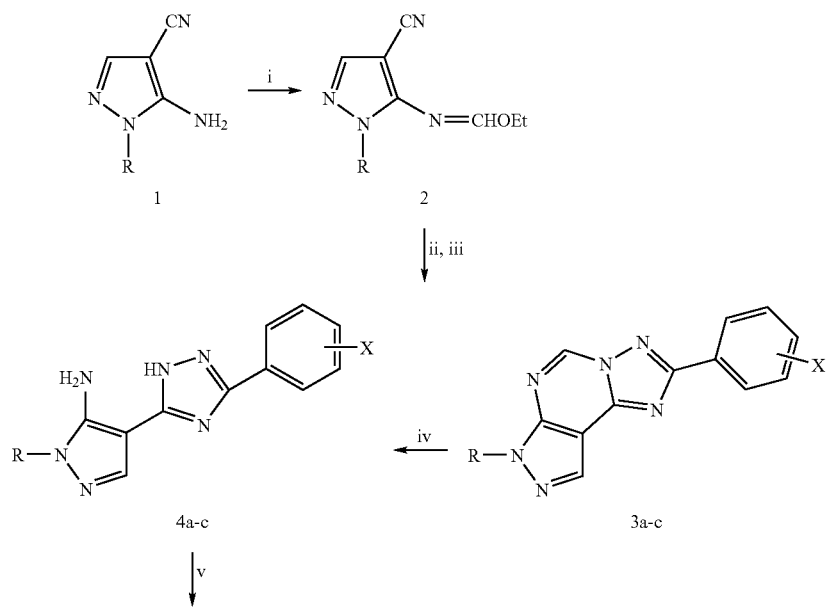

-continued

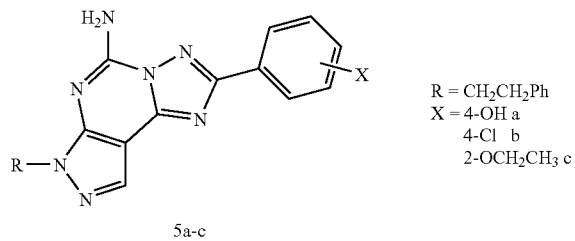

R = CH₂CH₂Ph
X = 4-OH a
   4-Cl b
   2-OCH₂CH₃ c

Reagents: (i) triethyl orthoformate, reflux; (ii) substituted benzoic acid hydrazides, 2-methoxyethanol; (iii) Ph₂O, 260° C.; (iv) 10% HCl; (v) cyanamide, 1-methyl-2-pyrrolidone, pTsOH, 140° C.

Scheme 2

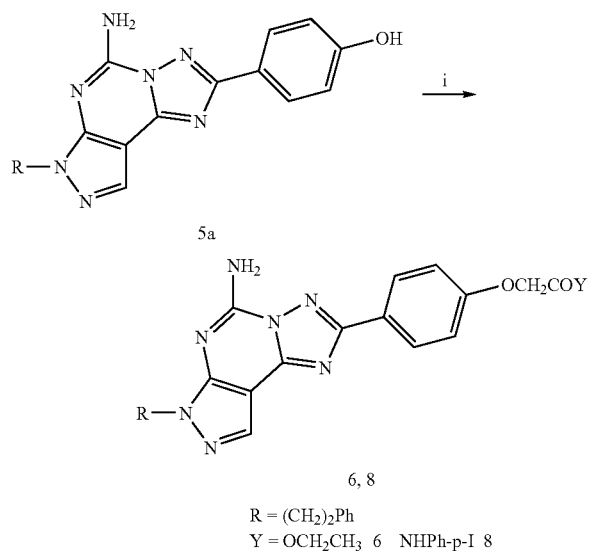

R = (CH₂)₂Ph
Y = OCH₂CH₃ 6    NHPh-p-I 8

Reagents: (i) 2-chloroacetylchloride, 2-chloro-N-(4-iodophenyl)acetamide, K₂CO₃, DMF, r.t.

Scheme 3

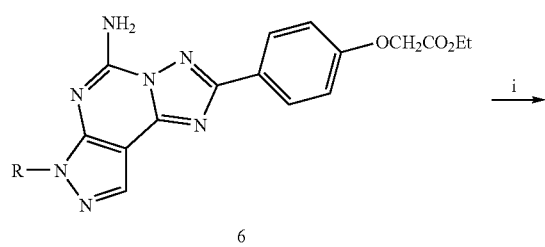

-continued

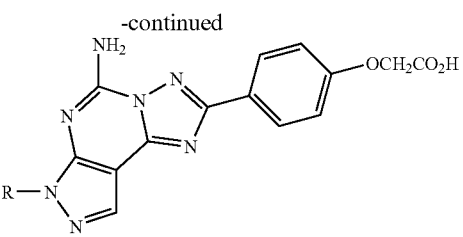

Reagents: (i) 10% HCl, dioxane, 60° C.

For the next steps of synthesis, the C-9 substituted compounds were synthesized according to the Gatta et al. procedure, which involved the transformation of pyrazoles 14 and 15 to the corresponding imidates 23 and 24 by refluxing in triethyl orthoformate. The imidates were reacted with 2-furoic acid hydrazide in refluxing 2-methoxyethanol to provide the pyrazolo[4,3-e]pyrimidine intermediates. The latter compounds were converted trough a thermal cyclization in diphenylether to the derivatives 29 and 30 in good overall yield.

Treatment of 29 and 30 with dilute hydrochloric acid at reflux induced pyrimidine ring opening to generate the 5-amino-4-(1H-1,2,4-triazol-5-yl)pyrazoles 35 and 37 in a very good yield.

These derivatives were converted into the final compounds 41 and 43 by reaction with an excess of cyanamide in N-1-methyl-2-pyrrolidone (NMP) at 140° C.

The reaction between malononitrile, carbondisulfide and 1-bromopropane gave the unsaturated intermediate 10 that was submitted to the same synthetic steps in order to obtain the final compound 42 (Scheme 4).

The compound 9, by reaction with amines A, B and C in ethanol, furnished the intermediates 11, 12 and 13 as reported in scheme 5.

The compounds 11–13 are then converted into aminocyanopyrazoles by cyclization with methylhydrazine in ethanol at reflux. The synthesis of the final compounds 38–40 was reached using the same synthetic steps for the obtaining of compounds 41 and 43.

The pyrazolo[4,3-e]-1,2,4-triazolo[1,5-c] pyrimidine derivatives 38, 40 and 41 were converted into the ureidic form by reaction with 4-methoxyphenylisocyanate and catalytic amount of TEA in order to obtain the compounds 44, 45 and 46 (Scheme 4 and 5). The tricyclic compounds 54 and 57 were converted into compounds 47–50 (Scheme 4 and 5) by reaction with acylchlorides in benzene and DMF as solvents. This permitted to introduce an amidic function in 5 position in order to evaluate the changing in affinity and selectivity versus the $A_3$ receptor subtype of the compounds obtained.

In the Scheme 6 the derivative 39 was converted into 52 by treatment with hydrobromic acid and iodic acid: the free hydroxyl group obtained was conceited to increase the water solubility of the final compound.

As reported in Scheme 7, the final compounds which posses a free amino function was transformed into a salt by treatment with a saturated methanolic solution of hydrochloric acid.

For the modifications at 5' position of the furyl ring of SCH 58261 and $C^9$ substituted compound 41, we apply the Mannich reaction as reported in scheme 8: appropriately tricyclic derivatives were reacted with N-methylpiperazine or morpholine and 36% aqueous formaldehyde in glacial acetic acid to gave the target compounds 51 and 57–58 in 20–30% yield.

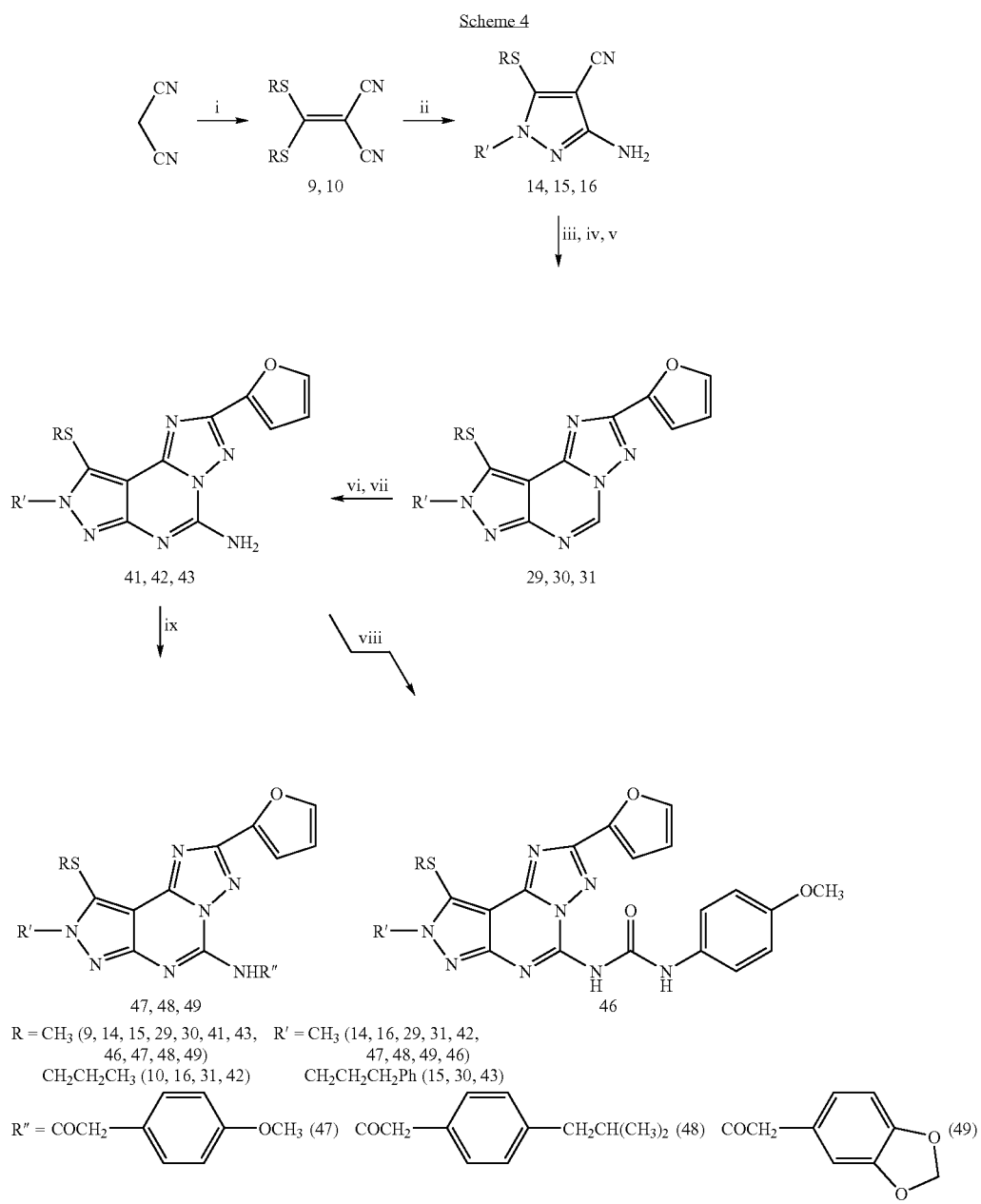

Reagents: (i) $CS_2$, $CH_3I$; (ii) (aryl)alkylhydrazine, reflux; (iii) $HC(OEt)_3$, reflux; (iv) 2-furoic acid hydrazide, $MeO(CH_2)_2OH$; (v) $Ph_2O$, 260° C.; (vi) 10% HCl; (vii) $NH_2CN$, pTsOH, 1-methyl-2-pyrrolidone, 140° C.; (viii) 4-methoxyphenylisocyanate, TEA; (ix) acylchlorides.

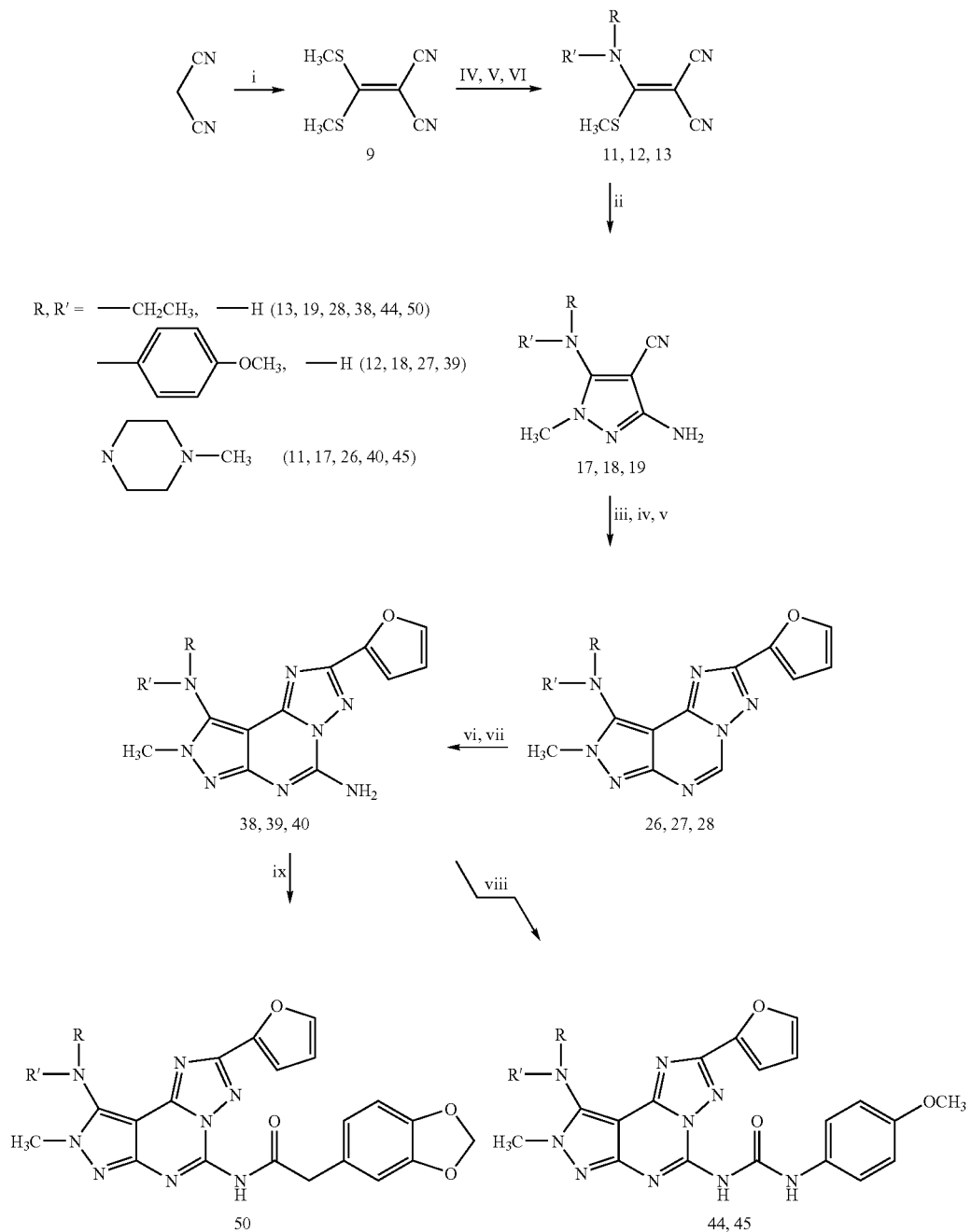

Scheme 5

Reagents: (i) $CS_2$, $CH_3I$; (ii) (aryl)alkylhydrazine, reflux; (iii) $HC(OEt)_3$, reflux; (iv) 2-furoic acid hydrazide, $MeO(CH_2)_2OH$; (v) $Ph_2O$, 260° C.; (vi) 10% HCl; (vii) $NH_2CN$, pTsOH, 1-methyl-2-pyrrolidone, 140° C.; (viii) 4-methoxyphenylisocyanate, TEA; (ix) acylchlorides.

IV: N-methylpiperazine; V: 4-methoxyaniline; VI: ethylamine
Scheme 6
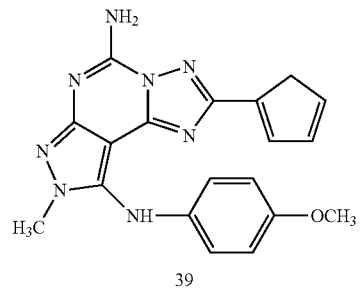
39
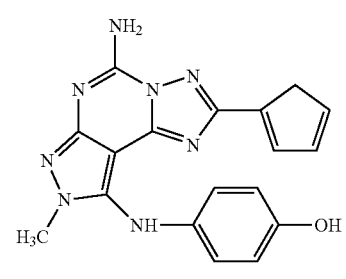
52
Reagents: (i) Acetic acid, Iodic acid, reflux.
Scheme 7
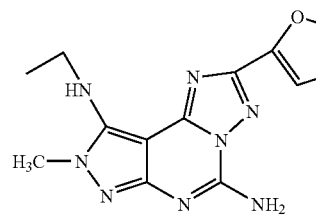
38
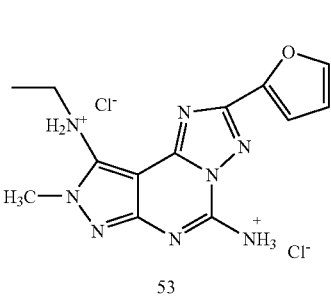
53
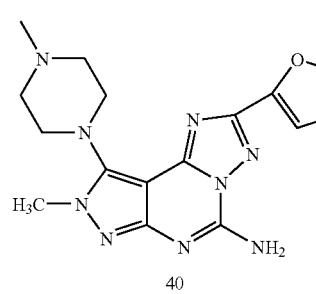
40
-continued
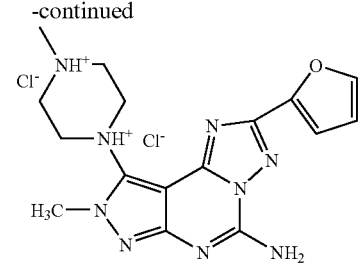
54
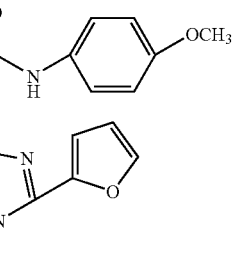
44
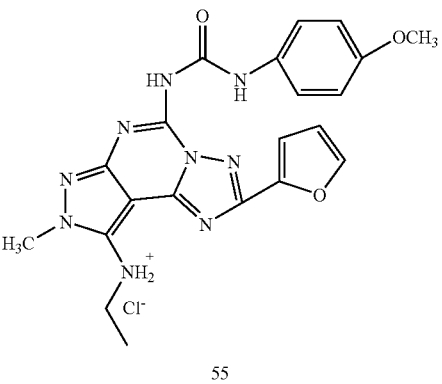
55
Reagents: (i) methanol, Hydrochloric acid.
Scheme 8
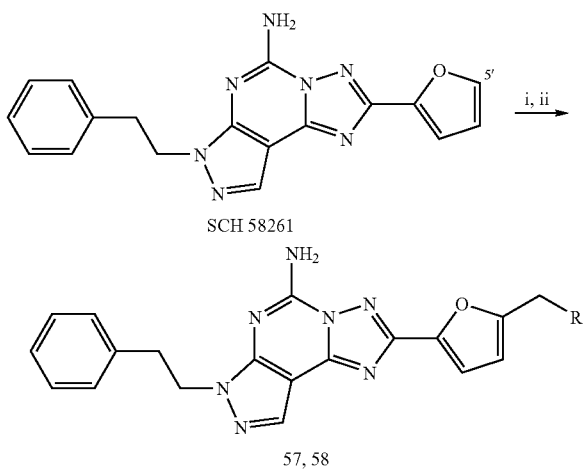
SCH 58261
57, 58

-continued

R = N-methylpyperazine (57), morpholine (58)

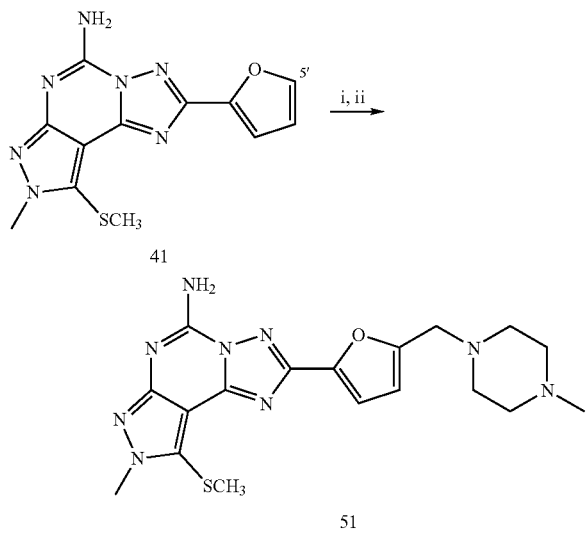

Reagents: (i) 36% aqueous formaldehyde, glacial acetic acid, (ii) N-methylpiperazine, The treatment of compounds 57, 58 and 61 with a saturated solution of hydrochloric acid in methanol gave the salts 56, 59 and 60 that had significant water solubility (Scheme 9).

Reagents: (i) methanol/hydrochloric acid, 0° C.

As discussed above, compounds disclosed herein are useful to treat a variety of diseases and disorders.

Compounds of the invention are suitable for modulating the response of adenosine receptors. Typically the compounds of the invention are suitable for use in modulating the response of one or more adenosine receptors selected from the $A_1$, $A_{2A}$, $A_{2B}$, or $A_3$ adenosine receptor subtypes. The invention provides a method for modulating adenosine activity in a mammal comprising administering to the mammal an effective amount of a compound of claim 1 which possess adenosine receptor antagonist activity.

The invention also includes treatment of neurodegenerative disorders and diseases. Typical subjects will include mammals, particularly humans, afflicted with neurodegenerative diseases such as Parkinson's disease, Huntington's disease, Amyotrophic Lateral Sclerosis, Alzheimer's disease, Down's Syndrome and Korsakoff's disease.

The invention also includes treatment of convulsant disorders, including treatment of a subject suffering from or susceptible to epilepsy.

Further preferred therapies include treatment or cardiac disorders and diseases, particularly including the treatment of congestive heart failure.

Further provided are antilipid treatment methods including reduction of free fatty acids, triglycerides, glucose; adjunct therapy in diabetes, including, insulin dependent and Scheme 9

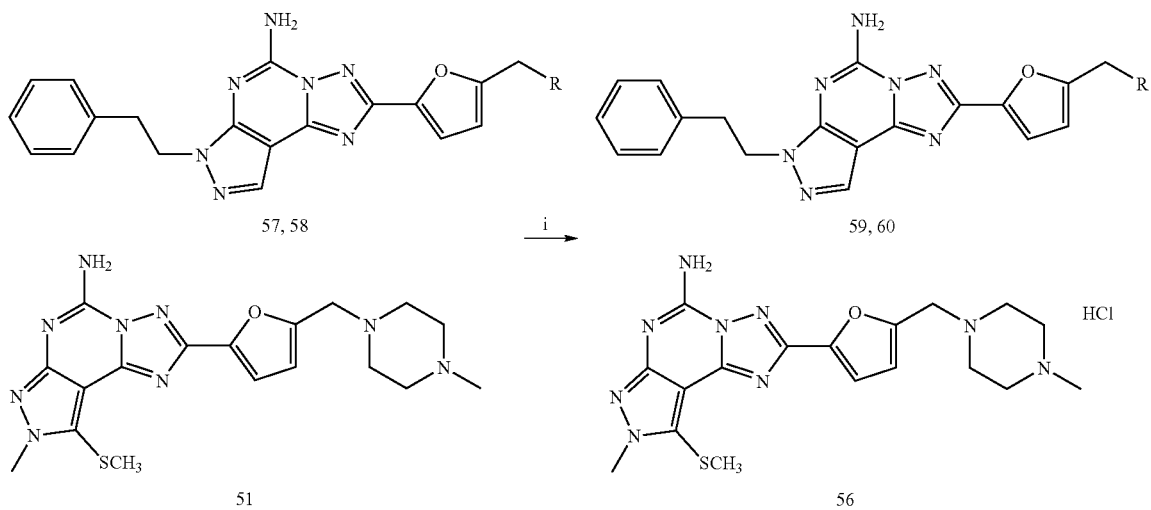

R = N-methylpyperazine HCl (59), morpholine HCl (60)

non-insulin dependent diabetes mellitus, stimulation of insulin secretion from the pancreas, and increase in tissue sensitivity to insulin.

The invention also includes methods for treatment of gastrointestinal disorders such as diarrhea, irritable bowel disease, irritable bowel syndrome, irritable bladder, and incontinence such as urge incontinence.

Also provided are methods for treatment of elevated intraocular pressure in a subject, and particularly treatment of prophylaxis of glaucoma.

The invention also provides treatment of a subject suffering from a sleep disorder, including sleep apnea.

The invention further provides treatment of inflammation, including actyue and chronic inflammatory conditions, e.g. arthritic conditions, ulcerative colitis, and the like.

The treatment methods of the invention also will be useful for treatment of mammals other than humans, including for veterinary applications such as to treat horses and livestock, e.g. cattle, sheep, cows, goats, swine and the like, and pets such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum cellular interstitial fluid, saliva, feces and urine) and cell and tissue samples of the above subjects will be suitable for use. Genetically modified cells and tissues, including modified cells and tissue of the above discussed subjects, also will be suitable for use.

A compound having a tricyclic pyrazolotriazolopyrimidine ring structure of the invention, including a compound of any of Formulae I through XI, may be administered to a subject as the sole therapeutic agent in a particular therapeutic regime. Alternatively, one or more compounds of the invention may be administered as a "cocktail" formulation with other therapeutics, i.e. coordinated administration of one or more compounds having a tricyclic pyrazolotriazolopyrimidine ring structure of the invention together with one or more other active therapeutics, particularly a coordinated administration with adenosine or an adenosine derivative.

Preferred formulations of the present invention for medical use comprise one or more compounds of the invention together with an acceptable carrier thereof and optionally other therapeutically active ingredients. The carrier should be pharmaceutically acceptable in the sense of being compatible with the other ingredients of the formulation and not deleterious to the recipient thereof.

The present invention, therefore, further provides a pharmaceutical formulation comprising one or more compounds of the above formulae together with a pharmaceutically acceptable carrier thereof.

The formulations include, but are not limited to, those suitable for oral, rectal, topical, intrathecal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients) may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations suitable for parenteral administration conveniently comprise sterile aqueous preparation of the active compound which is preferably isotonic with the blood of the recipient. Thus, such formulations may conveniently contain distilled water, 5% dextrose in distilled water or saline. Useful formulations also comprise concentrated solutions or solids containing the compound having a tricyclic pyrazolotriazolopyrimidine ring structure which upon dilution with an appropriate solvent give a solution suitable for parental administration above.

Formulations for parenteral administration or other administration route also may be admixed in an oil carrier, such as soybean oil.

Topical formulations include ointments, creams, gels and lotions which may be prepared by conventional methods known in the art of pharmacy. In addition to the ointment, cream gel, or lotion base and the active ingredient, such topical formulation may also contain preservatives, perfumes, and additional active pharmaceutical agents.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

See, in general, Remington's *Pharmaceutical Sciences* (Mack Publishing Co., Aston, Pa.), for a discussion of suitable administration formulations.

Preferred pharmaceutical compositions or kits of the invention will comprise one or more compounds having a tricyclic pyrazolotriazolopyrimidine ring structure of the invention packaged together with instructions (written) for therapeutic use of the one or more compounds for a disease or disorder as disclosed herein, e.g. written instructions for therapeutic use of the one or more compounds having a tricyclic pyrazolotriazolopyrimidine ring structure for pain management particularly treatment or prophylaxis of chronic pain including neuropathic pain; treatment of neurological injuries; treatment of neurodegenerative disease or convulsant disease or disorder; treatment of cardiac disorders or diseases; treatment of gastrointestinal disorders, treatment of elevated intraocular pressure such as may be associated with glaucoma; treatment of diabetes; and/or treatment of a sleep disorder.

Compounds of the invention are suitably administered to a subject in protonated and water-soluble form, e.g. as a pharmaceutically salt of an organic or inorganic acid, e.g. hydrochloride, sulfate, hemi-sulfate, phosphate, nitrate, acetate, oxalate, citrate, maleate, mesylate, etc., or as a salt of a suitable base or anion such as amines e.g. ammonium compounds such as tetramethylammonium, and other organic amines such as trimethylamine and triethylamine, and alkali or alkaline earth metal salts such as sodium, potassium, calcium, etc.

Compounds of the invention can be assessed for specific activity in a variety of protocols. As discussed above, a preferred protocol is by measurement of cAMP enhancement in CHO cells ("cAMP enhancement assay), as exemplified in Example 2, which follows.

The amount of compound of the present invention required to be effective as an modulator of an adenosine receptor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 pg/kg to about 100 mg/kg body weight per day, preferably in the range of about 1 mg/kg to about 30 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 75 mg to about 2200 mg per day, and a typical dose would be about 150 mg per day. If discrete multiple doses are indicated, treatment might typically be 50 mg of a compound of the present invention given 3 times per day.

All documents mentioned herein are incorporated herein by reference.

The following non-limiting examples are illustrative of the invention.

EXAMPLE 1

Pharmaceutical Formulations (A) Transdermal System—for 1000 patches

| Ingredients | Amount |
| --- | --- |
| Active compound | 100 g |
| Silicone fluid | 450 g |
| Colloidal silicon dioxide | 2 g |

The silicone fluid and active compound are mixed together and the colloidal silicon dioxide is added to increase viscosity. The material is then dosed into a subsequent heat sealed polymeric laminate comprised of the following: polyester release liner, skin contact adhesive composed of silicone or acrylic polymers, a control membrane which is a polyolefin, and an impermeable backing membrane made of a polyester multilaminate. The resulting laminated sheet is than cut into 10 sq. cm patches

| (B) Oral Tablet - For 1000 Tablets | |
| --- | --- |
| Ingredients | Amount |
| Active compound | 50 g |
| Starch | 50 g |
| Magnesium Stearate | 5 g |

The active compound and the starch are granulated with water and dried. Magnesium stearate is added to the dried granules and the mixture is thoroughly blended. The blended mixture is compressed into tablets.

| (C) Injection - for 1000, 1 mL Ampules | |
| --- | --- |
| Ingredients | Amount |
| Active compound | 10 g |
| Buffering Agents | q.s. |
| Propylene glycol | 400 mg |
| Water for injection | q.s. 1000 mL |

The active compound and buffering agents are dissolved in the propylene glycol at about 50° C. The water for injection is then added with stirring and the resulting solution is filtered, filled into ampules, sealed and sterilized by autoclaving.

| (D) Continuous Injection - for 1000 mL | |
| --- | --- |
| Ingredients | Amount |
| Active compound | 10 g |
| Buffering Agents | q.s. |
| Water for injection | q.s. 1000 mL |

EXAMPLE 2

Measurement of cAMP Enhancement in CHO Cells

Chinese hamster ovary cells expressing human recombinant $A_1$-adenosine receptors (CHO:huA1 cells) at a density of approximately 8000 fmol/mg protein are prepared as previously described (Kollias-Baker et al., (1997), *J. Pharmacol. Exp. Ther.* 281: 761–768) and aliquots of the cells at low passage numbers are frozen and stored in liquid nitrogen. When compounds are tested, an aliquot of CHO:huA1 cells is rapidly thawed after removal from liquid nitrogen, then grown in Ham's F12 culture medium with 10% fetal bovine serum and 0.5 mg/mL of antibiotic G-418 (Shryock, Ozeck, and Belardinelli (1998), *Mol. Pharmacol* 53: 886–893). Cells are passaged thrice weekly. Aliquots of cells are placed into 12-well plates with culture medium, serum, and antibiotic for 48 hours, by which time the cells have grown to a confluent monolayer.

Enhancement is measured as the action of a test compound at different concentrations (0.01, 0.1, 1 and 10 μM) to reduce the cAMP content of CHO:huA1 cells. To initiate an experiment, growth medium is removed from the 12-well plates and cells are washed once with warm Hanks' buffered saline. The wash solution is then removed and replaced with fresh Hanks' solution containing forskolin (1 μM), rolipram (20 μM), $N^6$-cyclopentyladenosine (CPA, 0.01 nM), adenosine deaminase (2 U/mL), and the test compound. Forskolin is used to stimulate the activity of adenylyl cyclase, rolipram to inhibit cAMP phosphodiesterase, adenosine deaminase to degrade endogenous adenosine, and CPA to cause a small increase of the number of activated adenosine receptors. After 6 min of incubation at 36° C. in the presence of test compound, the incubation solution is removed and hydrochloric acid (final concentration 50 mm) is added to terminate drug action. The content of cAMP in acidified extracts of cells is determined by radioimmunoassay as previously described (Kollias-Baker et al., (1997), *J. Pharmacol. Exp. Ther.* 281: 761–768). The effect of each test compound on cAMP content can be presented as a percentage of the value of cAMP content in the absence of drug (control, 100%).

EXAMPLE 3

Binding Activity for Compounds of the Invention Against $A_1$, $A_{2A}$, $A_{2B}$, $A_3$ Adenosine Receptors Table 2, 3, and 4 give the receptor affinity profile of compounds structurally modified synthesized and described in this work. The values of affinity are determined by receptor binding assay at human $A_1$, $A_{2A}$, $A_{2B}$ and $A_3$ adenosine receptor subtypes cloned in CHO and HEK-293 cells using [$^3$H]DPCPX, [$^3$H]SCH 58261, [$^3$H]DPCPX and [$^3$H]MRE 3008F20 respectively. The biological results of the new series of compounds 5a–8 modified in 2 position is showed in Table 2.

TABLE 2

Biological results of compounds 5a-8.

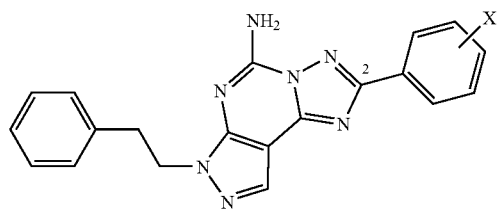

X = 4-OH, 4-Cl, 2-OEt, 4-OCH$_2$CO$_2$Et,
4-OCH$_2$CO$_2$H, 4-OCH$_2$CONHPh-p-I

| Compd | X | $A_1K_inM$ | $A_{2A}K_inM$ | $A_{2B}K_inM$ | $A_3K_inM$ |
| --- | --- | --- | --- | --- | --- |
| SCH 58261[a] | — | 121 | 2.3 | >1000 | >1000 |
| 5a[b] | 4-OH | >1000 | >1000 | >1000- | >1000 |
| 5b[b] | 4-Cl | >1000 | >1000 | >1000 | >1000 |
| 5c[b] | 2-OEt | >1000 | >1000 | >1000 | 348 |
| 6[b] | 4-OCH$_2$CO$_2$Et | >1000 | >1000 | >1000 | >1000 |
| 7[b] | 4-OCH$_2$CO$_2$H | >1000 | >1000 | >1000 | >1000 |
| 8[b] | OCH$_2$CONHPh-4'-1 | >1000 | >1000 | >1000 | >1000 |

[a]Displacement of [$^3$H]CHA binding ($A_1$) at rat cortical membrane, displacement of [$^3$H]CGS 21680 binding ($A_{2A}$) at rat striatal membranes and displacement of [$^{125}$I]AB MECA binding at human $A_3$ adenosine receptors expressed in HEK-293 cells.
[b]Displacement of [$^3$H]DPCPX binding ($A_1$, $A_{2B}$) at human $A_1$ and $A_{2B}$ adenosine receptors expressed in CHO and HEK-293 cells, displacement of [$^3$H]SCH58261 binding ($A_{2A}$) at human $A_{2A}$ adenosine receptors expressed in CHO cells and displacement of [$^3$H]MRE 3008F20 binding at human $A_3$ adenosine receptors expressed in CHO cells.

All the compounds synthesized were tested on all four adenosine receptor subtypes and the value of affinity are expressed in terms of SCH 58261 activity.

In general, we can note that the substitution of the furyl moiety with a substituted aromatic function causes a complete loss of affinity versus the $A_{2A}$ adenosine receptor subtype relative to the lead compound SCH 58261. This is supported by evidence that the furyl ring in the 2-position of the tricyclic structure is a necessary element to guarantee the activity of the molecule, probably because in this heterocycle is present an electronic condition favorable for interaction with the adenosine receptor.

Introduction of an ethoxy group in the ortho-position of the aromatic ring, in order to imitate the oxygen of the furan, was ineffective. The introduction of ester, acid or amide functions in the para position, in order to create an electronic condition for the formation of hydrogen bonds between the molecule and the adenosine receptor surface, was also ineffective.

Only the compound 5c show a poor affinity versus the $A_3$ adenosine receptor subtype, but a complete selectivity.

The biological results of the compounds modified in 9 position are showed in Table 3.

TABLE 3

| Comp | R | R$^1$ | R$^2$ | A$_1$ Ki nM$^a$ | A$_{2A}$ Ki nM$^b$ | A$_{2B}$ Ki nM$^c$ | A$_3$ Ki nM$^d$ |
|---|---|---|---|---|---|---|---|
| 38 | CH$_3$ | NHCH$_2$CH$_3$ | H | 50 | 10 | 81 | 225 |
| 39 | CH$_3$ | NH-Ph-p-OMe | H | 260 | — | — | — |
| 40 | CH$_3$ | N-Me-piperazine | H | 30 | 156 | 35 | — |
| 41 | CH$_3$ | SCH$_3$ | H | 8.4 | 1.2 | 10.3 | 35 |
| 42 | CH$_3$ | S(CH$_2$)$_2$CH$_3$ | H | 9 | 2.1 | 69 | 224 |
| 43 | Ph(CH$_2$)$_3$ | SCH$_3$ | H | 175 | 22 | 31 | — |
| 44 | CH$_3$ | NHCH$_2$CH$_3$ | CONHPh-p-OMe | 150 | -21 | 37 | 17 |
| 45 | CH$_3$ | N-Me-piperazine | CONHPh-p-OMe | 316 | — | 26 | — |
| 46 | CH$_3$ | SCH$_3$ | CONHPh-p-OMe | 70 | 3.1 | 24 | 212 |
| 47 | CH$_3$ | SCH$_3$ | COCHPh-p-OMe | 80 | 15 | 45 | — |
| 48 | CH$_3$ | SCH$_3$ | COCH$_2$Ph-p-isobutyl | 780 | 50 | 190 | — |
| 49 | CH$_3$ | SCH$_3$ | COCH$_2$Ph-3,4-Medioxy | 70 | 4.1 | 30 | 110 |
| 50 | CH$_3$ | NHCH$_2$CH$_3$ | COCH$_2$Ph-3,4-Medioxy | 136 | 61 | 65 | 183 |
| 52 | CH$_3$ | NH-Ph-p-OH | H | 666 | — | — | 308 |
| 53 | CH$_3$ | NHCH$_2$CH$_3$HCl | H | 41 | 10 | 36 | 25 |
| 54 | CH$_3$ | N-Me-piperazine 2HCl | H | 48 | 135 | 12 | — |
| 55 | CH$_3$ | NHCH$_2$CH$_3$HCl | CONHPh-p-OMe | 100 | 16 | 23 | 9 |

$^a$Displacement of [$^3$H]DPCPX binding at human A$_1$ adenosine receptors expressed in CHO cells.
$^b$Displacement of [$^3$H]SCH58261 binding at human A$_{2A}$ adenosine receptors expressed in CHO cells.
$^c$Displacement of [$^3$H]DPCPX binding at human A$_{2B}$ adenosine receptors expressed in HEK-293 cells.
$^d$Displacement of [$^3$H]MRE 3008F20 binding at human A$_3$ adenosine receptors expressed in CHO cells.

As shown in the table, the introduction of a substituent in 9-position, instead of a hydrogen that is present in the lead compounds SCH 58261 and in MRE series, determines a loss of selectivity but a maintenance of receptor affinity.

In general the thiomethyl group in the 9-position is the best tolerated and in the 8-position the methyl group is better tolerated than phenylpropyl substituent by A$_{2A}$ adenosine receptor subtype.

The compound 41, which possesses a free amino group in the 5-position, shows a good affinity for A$_{2A}$ adenosine receptor but, unfortunately, low selectivity; the transformation of the amino group into a ureidic function (compound 46) or amidic functions (compounds 47, 48 and 49) maintains A$_{2A}$ affinity, but the interaction with the A$_3$ adenosine receptor subtype is decreased.

In this case we can say that the presence of a substituent in 9-position doesn't permit the A$_3$-interaction ever obtained by the functionalization of the free amino group in 5-position of the pyrazolotriazolopyrimidine structure.

The substitution of the thiomethyl group by a thiopropyl group in the 9-position maintains the A$_{2A}$ affinity and increases the selectivity (compound 42), but the introduction of a phenylpropyl group in the 8-position, instead of a methyl group (compound 43), determines a decrease of A$_{2A}$ interaction.

Contrary the compound 38, which possesses an aminoethyl group in the 9-position, shows a good affinity on A$_{2A}$ adenosine receptor subtype and, in this case, the functionalization of amino group into p-methoxyphenylurea determines a decrease of A$_{2A}$ affinity but a good increase in A$_3$ affinity (compound 44).

The interaction with the A$_3$ receptor is also increased by the salification of this molecule (compound 55) probably due to the complete water solubility. Also in this compound the selectivity versus the other adenosine receptor subtype is very low.

The introduction in 9-position of other amino functions, like p-methoxyphenylamino, N-methylpiperazine or p-hydroxyphenylamino (compounds 39, 40 and 52) was useless for the A$_{2A}$ interaction, and also the functionalization of amino group of compound 40 into urea for A$_3$ interaction. This may be due to an important steric hindrance of the radical introduced.

We can conclude that the modifications in 9-position permit to maintain the antagonistic activity, better tolerated by small groups introduced like thiomethyl or ethylamino, but induce a significant loss of selectivity.

The lead compound SCH 58261 and the compound 41 who displayed improved antagonistic activity on A$_{2A}$ adenosine receptor subtype, were modified in 2'-position of the furyl ring by Mannich reaction, introducing cycloamino methyl functions. These functions, easy salified, permitted to increase the water solubility of the resultant compounds and to observe the variations of affinity and selectivity versus A$_{2A}$ adenosine receptor subtype.

By this transformation we obtained enhanced water solubility but a complete loss of affinity versus all the types of adenosine receptors (see Table 4). Also for compounds 5a–8 we can confirm that the furyl moiety is a necessary element for receptor interaction and any kind of modifications are allowed.

TABLE 4

| Compd | R | A$_1$ K$_i$ nM$^a$ | A$_{2A}$ K$_i$ nM$^b$ | A$_{2B}$ K$_i$ nM$^c$ | A$_3$ K$_i$ nM$^d$ |
|---|---|---|---|---|---|
| 56 | N-methyl-piperazine | >1000 | >1000 | >1000 | >1000 |
| 59 | N-methyl-piperazine | >1000 | >1000 | >1000 | >1000 |
| 60 | Morpholine | >1000 | >1000 | >1000 | >1000 |

$^a$Displacement of [$^3$H]DPCPX binding at human A$_1$ adenosine receptors expressed in CHO cells.
$^b$Displacement of [$^3$H]SCH58261 binding at human A$_{2A}$ adenosine receptors expressed in CHO cells.
$^c$Displacement of [$^3$H]DPCPX binding at human A$_{2B}$ adenosine receptors expressed in HEK-293 cells.
$^d$Displacement of [$^3$H]MRE 3008F20 binding at human A$_3$ adenosine receptors expressed in CHO cells.

The invention has been described in detail with reference to preferred embodiments thereof. However, it will be appreciated that those skilled in the art, upon consideration of the disclosure, may make modifications and improvements within the spirit and scope of the invention.

What is claimed is:

1. A compound of any one of the following Formula IX or X:

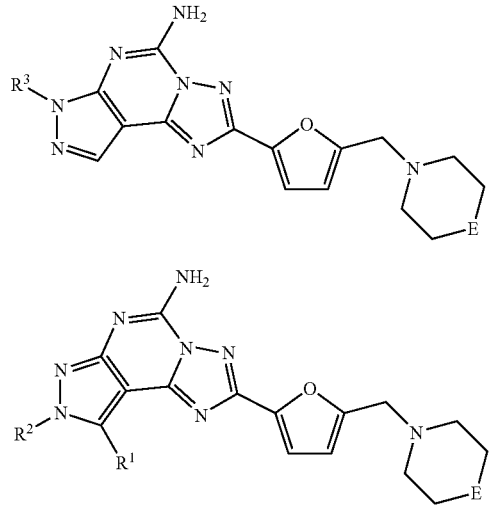

wherein:
R¹ is selected from the group consisting of hydrogen, $C_{1-6}$alkylamino, di($C_{1-6}$) alkylamino, and $C_{1-6}$alylthio;
R² is selected from optionally substituted $C_{1-6}$alkyl and optionally substituted $C_{7-12}$aralkyl;
R³ is selected from the group consisting of optionally substituted a $C_{1-6}$alkyl, optionally substituted $C_{7-12}$aralkyl, and optionally substituted $C_{2-6}$alkanoyl;
E is O or N—$C_{1-6}$alkyl; and pharmaceutically acceptable salt thereof.

2. A compound that is:
4-(5-Amino-7-phenethyl-7H-pyrazolo[4,3-e][1,2,4]triazolo[1,5-c]pyrimidin-2-yl)-phenol;
2-(4-Chloro-phenyl)-7-phenethyl-7H-pyrazolo[4,3-e][1,2,4]triazolo[1,5-c]pyrimidin-5-ylamine;
2-(4-Ethoxy-phenyl)-7-phenethyl-7H-pyrazolo[4,3-e][1,2,4]triazolo[1,5-c]pyrimidin-5-ylamine; [4-(5-Amino-7-phenethyl-7H-pyrazolo[4,3-e][1,2,4]triazolo[1,5-c]pyrimidin-2-yl)-phenoxy]-acetic acid ethyl ester;
[4-(5-Amino-7-phenethyl-7H-pyrazolo[4,3-e][1,2,4]triazolo[1,5-c]pyrimidin-2-yl)-phenoxy]-acetic acid;
2-[4-(5-Amino-7-phenethyl-7H-pyrazolo[4,3-e][1,2,4]triazolo[1,5-c]pyrimidin-2-yl)-phenoxy]-N-(4-iodo-phenyl)-acetamide;
N9-Ethyl-2-furan-2-yl-8-methyl-8H-pyrazolo[4,3-e][1,2,4]triazolo[1,5-c]pyrimidine-5,9-diamine;
N9-Ethyl-2-furan-2-yl-8-methyl-8H-pyrazolo[4,3-e][1,2,4]triazolo[1,5-c]pyrimidine-5,9-diamine hydrochloride salt;
2-Furan-2-yl-N-9-(4-methoxy-phenyl)-8-methyl-8H-pyrazolo[4,3-e][1,2,4]triazolo[1,5-c]pyrimidine-5,9-diamine;
2-Furan-2-yl-8-methyl-9-(4-methyl-piperazin-1-yl)-8H-pyrazolo[4,3-e][1,2,4]triazolo[1,5-c]pyrimidin-5-ylamine;
2-Furan-2-yl-8-methyl-9-(4-methyl-piperazin-1-yl)-8H-pyrazolo[4,3-e][1,2,4]triazolo[1,5-c]pyrimidin-5-ylamine dihydrochloride salt;
2-Furan-2-yl-8-methyl-9-methylsulfanyl-8H-pyrazolo[4,3-e][1,2,4]triazolo[1,5-c]pyrimidin-5-ylamine;
2-Furan-2-yl-8-methyl-9-propylsulfanyl-8H-pyrazolo[4,3-e][1,2,4]triazolo[1,5-c]pyrimidin-5-ylamine;
2-Furan-2-yl-9-methylsulfanyl-8-(3-phenyl-propyl)-8H-pyrazolo[4,3-e][1,2,4]triazolo[1,5-c]pyrimidin-5-ylamine;
1-(9-Ethylamino-2-furan-2-yl-8-methyl-8H-pyrazolo[4,3-e][1,2,4]triazolo[1,5-c]pyrimidin-5-yl)-3-(4-methoxy-phenyl)-urea;
1-(9-Ethylamino-2-furan-2-yl-8-methyl-8H-pyrazolo[4,3-e][1,2,4]triazolo[1,5-c]pyrimidin-5-yl)-3-(4-methoxy-phenyl)-urea hydrochloride salt;
1-[2-Furan-2-yl-8-methyl-9-(4-methyl-piperazin-1-yl)-8H-pyrazolo[4,3-e][1,2,4]triazolo[1,5-c]pyimidin-5-yl]-3-(4-methoxy-phenyl)-urea;
1-(2-Furan-2-yl-8-methyl-9-methylsulfanyl-8H-pyrazolo[4,3-e][1,2,4]triazolo[1,5-c]pyrimidin-5-yl)-3-(4-methoxy-phenyl)-urea;
N-(2-Furan-2-yl-8-methyl-9-methylsulfanyl-8H-pyrazolo[4,3-e][1,2,4]triazolo[1,5-c]pyrimidin-5-yl)-2-(4-methoxy-phenyl)-acetamide;
N-(2-Furan-2-yl-8-methyl-9-methylsulfanyl-8H-pyrazolo[4,3-e][1,2,4]triazolo[1,5-c]pyrimidin-5-yl)-2-(4-isobutyl-phenyl)-acetamide;
2-Benzo[1,3]dioxol-5-yl-N-(2-furan-2-yl-8-methyl-9-methylsulfanyl-8H-pyrazolo[4,3-e][1,2,4]triazolo[1,5-c]pyrimidin-5-yl)-acetamide;
2-Benzo[1,3]dioxol-5-yl-N-(9-ethylamino-2-furan-2-yl-8-methyl-8H-pyrazolo[4,3-e][1,2,4]triazolo[1,5-c]pyrimidin-5-yl)-acetamide;
4-(5-Amino-2-furan-2-yl-8-methyl-8H-pyrazolo[4,3-e][1,2,4]triazolo[1,5-c]pyrimidin-9-ylamino)-phenol;
8-Methyl-2-[5-(4-methyl-piperazin-1-ylmethyl)-furan-2-yl]-9-methylsulfanyl-8H-pyrazolo[4,3-e][1,2,4]triazolo[1,5-c]pyrimidin-5-ylamine;
8-Methyl-9-methylsulfanyl-2-(5-morpholin-4-ylmethyl-furan-2-yl)-8H-pyrazolo[4,3-e][1,2,4]triazolo[1,5-c]pyrimidin-5-ylamine; or a pharmaceutically acceptable salt thereof.

3. A pharmaceutical composition comprising a pharmaceutically acceptable carrier and one or more compounds of any one of claims 1 or 2.

* * * * *

UNITED STATES PATENT AND TRADEMARK OFFICE
CERTIFICATE OF CORRECTION

PATENT NO.       : 7,064,204 B2                                              Page 1 of 2
APPLICATION NO.  : 10/452788
DATED            : June 20, 2006
INVENTOR(S)      : Pier Giovanni Baraldi and Pier Andrea Borea It is certified that error appears in the above-identified patent and that said Letters Patent is hereby corrected as shown below:

Column 27, lines 7 to 28, the structures in Scheme 6 should appear as follows:

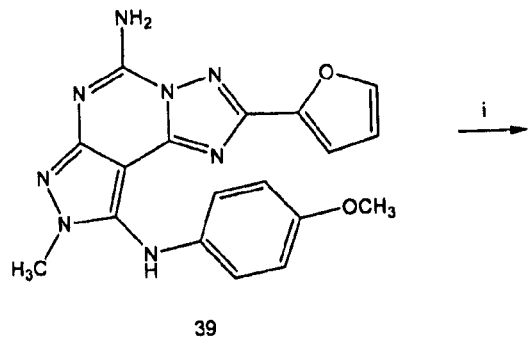
39

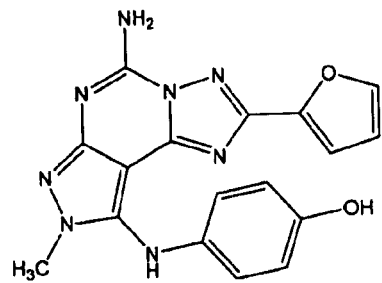
52

UNITED STATES PATENT AND TRADEMARK OFFICE
CERTIFICATE OF CORRECTION

PATENT NO. : 7,064,204 B2
APPLICATION NO. : 10/452788
DATED : June 20, 2006
INVENTOR(S) : Pier Giovanni Baraldi and Pier Andrea Borea It is certified that error appears in the above-identified patent and that said Letters Patent is hereby corrected as shown below:

Column 39, lines 17 to 25, the structure of a compound of Formula X should appear as follows:

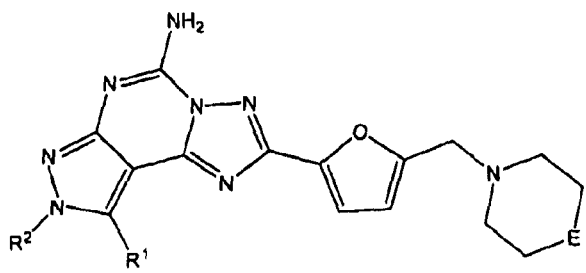

Signed and Sealed this

Eighth Day of July, 2008

JON W. DUDAS
*Director of the United States Patent and Trademark Office*